(12) United States Patent
Kleshinski et al.

(10) Patent No.: US 12,263,076 B2
(45) Date of Patent: *Apr. 1, 2025

(54) MULTI-ACCESS INTRAPROCEDURAL EMBOLIC PROTECTION DEVICE

(71) Applicant: Emboline, Inc., Santa Cruz, CA (US)

(72) Inventors: Stephen J. Kleshinski, Fremont, CA (US); Scott M. Russell, Santa Cruz, CA (US); Amir Belson, Savyon (IL)

(73) Assignee: Emboline, Inc., Santa Cruz, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/183,067

(22) Filed: Mar. 13, 2023

(65) Prior Publication Data

US 2023/0210650 A1    Jul. 6, 2023

Related U.S. Application Data

(60) Continuation of application No. 17/858,637, filed on Jul. 6, 2022, which is a continuation of application
(Continued)

(51) Int. Cl.
    *A61F 2/01*    (2006.01)
    *A61F 2/24*    (2006.01)

(52) U.S. Cl.
    CPC ............ *A61F 2/014* (2020.05); *A61F 2/0105* (2020.05); *A61F 2/013* (2013.01); *A61F 2/011* (2020.05);
(Continued)

(58) Field of Classification Search
    CPC ........ A61F 2/013; A61F 2/0105; A61F 2/011; A61F 2/014; A61F 2/2427; A61F 2002/016; A61F 2230/0069; A61F 2250/0069
    See application file for complete search history.

(56) References Cited

U.S. PATENT DOCUMENTS

| 4,723,549 A | 2/1988 | Wholey et al. |
| 4,790,809 A | 12/1988 | Kuntz |

(Continued)

FOREIGN PATENT DOCUMENTS

| CA | 2575865 A1 | 1/1998 |
| CA | 2609800 A1 | 1/2007 |

(Continued)

OTHER PUBLICATIONS 16882367.2 European Search Opinion and Extended European Search Report dated Aug. 7, 2019.
(Continued)

*Primary Examiner* — Brooke Labranche
(74) *Attorney, Agent, or Firm* — Shay Glenn LLP

(57) ABSTRACT

An embolic protection device comprises a tubular filter body attached to a sheath. The tubular filter body has an open upstream end and a generally closed downstream end for capturing emboli. A self-opening passage through the emboli capture end of the tubular filter body allows multiple catheters to be advanced from the sheath or otherwise into the filter body simultaneously or sequentially. The sheath is attached to a peripheral support structure near the emboli capture end of the filter body to facilitate deployment and retrieval of the filter body through a restraining delivery catheter.

18 Claims, 24 Drawing Sheets

Related U.S. Application Data

No. 16/808,859, filed on Mar. 4, 2020, now Pat. No. 11,399,927, which is a division of application No. 15/137,924, filed on Apr. 25, 2016, now Pat. No. 10,617,509.

(60) Provisional application No. 62/297,053, filed on Feb. 18, 2016, provisional application No. 62/294,018, filed on Feb. 11, 2016, provisional application No. 62/272,643, filed on Dec. 29, 2015.

(52) U.S. Cl.
CPC ....... *A61F 2002/016* (2013.01); *A61F 2/2427* (2013.01); *A61F 2230/0069* (2013.01); *A61F 2250/0069* (2013.01)

(56) References Cited

U.S. PATENT DOCUMENTS

| | | |
|---|---|---|
| 5,108,419 A | 4/1992 | Reger et al. |
| 5,197,485 A | 3/1993 | Grooters |
| 5,554,183 A | 9/1996 | Nazari |
| 5,643,227 A | 7/1997 | Stevens |
| 5,769,816 A | 6/1998 | Barbut et al. |
| 5,769,819 A | 6/1998 | Schwab et al. |
| 5,797,880 A | 8/1998 | Erskine |
| 5,800,525 A | 9/1998 | Bachinski et al. |
| 5,807,327 A | 9/1998 | Green et al. |
| 5,928,261 A | 7/1999 | Ruiz |
| 6,013,051 A | 1/2000 | Nelson |
| 6,083,239 A | 7/2000 | Addis |
| 6,117,154 A | 9/2000 | Barbut et al. |
| 6,120,534 A | 9/2000 | Ruiz |
| 6,139,517 A | 10/2000 | Macoviak et al. |
| 6,152,144 A | 11/2000 | Lesh et al. |
| 6,245,012 B1 | 6/2001 | Kleshinski |
| 6,254,563 B1 | 7/2001 | Macoviak et al. |
| 6,254,633 B1 | 7/2001 | Pinchuk et al. |
| 6,258,120 B1 | 7/2001 | McKenzie et al. |
| 6,348,063 B1 | 2/2002 | Yassour et al. |
| 6,355,051 B1 | 3/2002 | Sisskind et al. |
| 6,361,545 B1 | 3/2002 | Macoviak et al. |
| 6,371,935 B1 | 4/2002 | Macoviak et al. |
| 6,391,044 B1 | 5/2002 | Yadav et al. |
| 6,461,370 B1 | 10/2002 | Gray et al. |
| 6,499,487 B1 | 12/2002 | McKenzie et al. |
| 6,511,496 B1 | 1/2003 | Huter et al. |
| 6,537,297 B2 | 3/2003 | Tsugita et al. |
| 6,547,760 B1 | 4/2003 | Samson et al. |
| 6,682,543 B2 | 1/2004 | Barbut et al. |
| 6,692,513 B2 | 2/2004 | Streeter et al. |
| 6,695,864 B2 | 2/2004 | Macoviak et al. |
| 6,709,415 B2 | 3/2004 | Navia et al. |
| 6,712,834 B2 | 3/2004 | Yassour et al. |
| 6,746,469 B2 | 6/2004 | Mouw |
| 6,808,520 B1 | 10/2004 | Fourkas et al. |
| 7,044,958 B2 | 5/2006 | Douk et al. |
| 7,229,463 B2 | 6/2007 | Sutton et al. |
| 7,232,453 B2 | 6/2007 | Shimoin |
| 7,235,060 B2 | 6/2007 | Kraus |
| 7,537,600 B2 | 5/2009 | Eskuri |
| 7,758,606 B2 | 7/2010 | Streeter et al. |
| 7,766,932 B2 | 8/2010 | Melzer et al. |
| 7,959,662 B2 | 6/2011 | Erbel et al. |
| 8,052,717 B2 | 11/2011 | Mujkanovic |
| 8,114,114 B2 | 2/2012 | Belson |
| 8,123,779 B2 | 2/2012 | Demond et al. |
| 8,298,258 B2 | 10/2012 | Anderson et al. |
| 8,308,754 B2 | 11/2012 | Belson |
| 8,337,519 B2 | 12/2012 | Wasicek |
| 8,382,788 B2 | 2/2013 | Galdonik et al. |
| 8,383,788 B2 | 2/2013 | Oliviero |
| 8,414,482 B2 | 4/2013 | Belson |
| 8,419,677 B2 | 4/2013 | Ducharme et al. |
| 8,420,902 B2 | 4/2013 | Gilsinger |
| 8,430,904 B2 | 4/2013 | Belson |
| 8,679,149 B2 | 3/2014 | Belson |
| 8,728,114 B2 | 5/2014 | Belson |
| 8,740,930 B2 | 6/2014 | Goodwin |
| 8,968,354 B2 | 3/2015 | Wang et al. |
| 9,144,485 B2 | 9/2015 | Bergheim |
| 9,427,252 B2 | 8/2016 | Sos |
| 9,492,265 B2 | 11/2016 | Russell et al. |
| 9,744,023 B2 | 8/2017 | Wang et al. |
| 9,770,318 B2 | 9/2017 | Belson |
| 9,827,085 B2 | 11/2017 | Russell et al. |
| 9,877,821 B2 | 1/2018 | Russell et al. |
| 10,016,267 B2 | 7/2018 | Belson |
| 10,166,094 B2 | 1/2019 | Russell et al. |
| 10,617,507 B2 | 4/2020 | Belson |
| 10,617,509 B2 | 4/2020 | Kleshinski et al. |
| 10,617,510 B2 | 4/2020 | Russell et al. |
| 10,736,728 B2 | 8/2020 | Belson |
| 10,870,340 B2 | 12/2020 | Acikgoez et al. |
| 10,881,494 B2 | 1/2021 | Belson |
| 10,939,987 B2 | 3/2021 | Belson |
| 11,051,927 B2 | 7/2021 | Russell et al. |
| 11,304,792 B2 | 4/2022 | Russell et al. |
| 11,399,927 B2 | 8/2022 | Kleshinski et al. |
| 2001/0044632 A1 | 11/2001 | Daniel et al. |
| 2002/0004667 A1 | 1/2002 | Adams et al. |
| 2002/0045916 A1 | 4/2002 | Gray et al. |
| 2002/0058964 A1 | 5/2002 | Addis |
| 2002/0111648 A1 | 8/2002 | Kusleika et al. |
| 2002/0128680 A1 | 9/2002 | Addis |
| 2002/0161394 A1 | 10/2002 | Macoviak et al. |
| 2003/0040736 A1 | 2/2003 | Stevens |
| 2003/0040772 A1 | 2/2003 | Hoyodoh et al. |
| 2003/0100940 A1 | 5/2003 | Yodfat |
| 2003/0125765 A1 | 7/2003 | Blackledge et al. |
| 2003/0144686 A1 | 7/2003 | Martinez et al. |
| 2003/0176884 A1 | 9/2003 | Berrada et al. |
| 2003/0187474 A1 | 10/2003 | Keegan et al. |
| 2003/0208224 A1 | 11/2003 | Broome |
| 2004/0034380 A1 | 2/2004 | Woolfson et al. |
| 2004/0073253 A1 | 4/2004 | Morrill et al. |
| 2004/0138692 A1 | 7/2004 | Phung et al. |
| 2004/0225354 A1 | 11/2004 | Allen et al. |
| 2005/0010246 A1 | 1/2005 | Streeter et al. |
| 2005/0060017 A1 | 3/2005 | Fischell et al. |
| 2005/0075724 A1 | 4/2005 | Svanidze et al. |
| 2005/0137688 A1 | 6/2005 | Salahieh et al. |
| 2005/0137696 A1 | 6/2005 | Salahieh et al. |
| 2005/0159773 A1 | 7/2005 | Broome et al. |
| 2005/0203569 A1 | 9/2005 | Kusleika et al. |
| 2005/0283186 A1 | 12/2005 | Berrada et al. |
| 2005/0283231 A1 | 12/2005 | Haug et al. |
| 2006/0100658 A1 | 5/2006 | Obana et al. |
| 2006/0129181 A1 | 6/2006 | Callol et al. |
| 2006/0135977 A1 | 6/2006 | Thompson et al. |
| 2006/0173490 A1 | 8/2006 | Lafontaine et al. |
| 2006/0287668 A1 | 12/2006 | Fawzi et al. |
| 2006/0293706 A1 | 12/2006 | Shimoin |
| 2007/0027534 A1 | 2/2007 | Bergheim et al. |
| 2007/0060944 A1 | 3/2007 | Boldenow et al. |
| 2007/0073246 A1 | 3/2007 | Simon |
| 2007/0073332 A1 | 3/2007 | Miller et al. |
| 2008/0027481 A1 | 1/2008 | Gilson et al. |
| 2008/0234722 A1 | 9/2008 | Bonnette et al. |
| 2009/0149881 A1 | 6/2009 | Vale et al. |
| 2009/0254172 A1 | 10/2009 | Grewe |
| 2010/0010535 A1 | 1/2010 | Mujkanovic |
| 2010/0106180 A1 | 4/2010 | Strother et al. |
| 2010/0191326 A1 | 7/2010 | Alkhatib |
| 2010/0262219 A1 | 10/2010 | Frimerman |
| 2010/0274277 A1 | 10/2010 | Eaton |
| 2010/0286768 A1 | 11/2010 | Alkhatib |
| 2010/0305604 A1 | 12/2010 | Pah |
| 2010/0312268 A1 | 12/2010 | Belson |
| 2012/0016408 A1 | 1/2012 | Barbut et al. |
| 2012/0109056 A1 | 5/2012 | Rasmussen |
| 2012/0172915 A1 | 7/2012 | Fifer et al. |
| 2012/0172918 A1 | 7/2012 | Fifer et al. |

(56) References Cited

U.S. PATENT DOCUMENTS

| | | |
|---|---|---|
| 2012/0271340 A1 | 10/2012 | Castellano et al. |
| 2012/0271341 A1 | 10/2012 | Hill et al. |
| 2012/0330346 A1 | 12/2012 | Frimerman |
| 2012/0330348 A1 | 12/2012 | Strauss et al. |
| 2013/0046330 A1 | 2/2013 | McIntosh et al. |
| 2013/0096606 A1 | 4/2013 | Bruchman et al. |
| 2013/0245669 A1 | 9/2013 | Basu et al. |
| 2013/0267993 A1 | 10/2013 | Carpenter |
| 2014/0000091 A1 | 1/2014 | Angel et al. |
| 2014/0058372 A1 | 2/2014 | Belson |
| 2014/0214069 A1 | 7/2014 | Franklin |
| 2014/0249568 A1 | 9/2014 | Adams et al. |
| 2014/0277096 A1 | 9/2014 | Richter et al. |
| 2014/0343595 A1 | 11/2014 | Monstadt et al. |
| 2015/0006607 A1 | 1/2015 | E'Wanyou |
| 2015/0032120 A1 | 1/2015 | Janardhan et al. |
| 2015/0320540 A1 | 11/2015 | Belson |
| 2015/0342717 A1 | 12/2015 | O'Donnell et al. |
| 2015/0366650 A1 | 12/2015 | Zi et al. |
| 2016/0193045 A1 | 7/2016 | Pollak |
| 2016/0296315 A1 | 10/2016 | Yachia et al. |
| 2016/0317277 A1 | 11/2016 | Carpenter et al. |
| 2016/0367285 A1* | 12/2016 | Sos ................. A61B 17/221 |
| 2018/0206970 A1 | 7/2018 | Eggert et al. |
| 2019/0015152 A1 | 1/2019 | Howard et al. |
| 2020/0281717 A1 | 9/2020 | Spence |
| 2021/0161638 A1 | 6/2021 | Belson |
| 2021/0315680 A1 | 10/2021 | Russell et al. |
| 2022/0008186 A1 | 1/2022 | Belson |
| 2022/0265414 A1 | 8/2022 | Russell et al. |
| 2023/0091397 A1 | 3/2023 | Kleshinski et al. |
| 2023/0293282 A1 | 9/2023 | Kleshinski et al. |
| 2023/0346536 A1 | 11/2023 | Kleshinski et al. |

FOREIGN PATENT DOCUMENTS

| | | |
|---|---|---|
| CN | 1278713 A | 1/2001 |
| CN | 1331956 A | 1/2002 |
| CN | 101351242 | 1/2009 |
| CN | 201798779 U | 4/2011 |
| CN | 102186427 A | 9/2011 |
| CN | 102256566 A | 11/2011 |
| CN | 102811679 A | 12/2012 |
| CN | 102973332 A | 3/2013 |
| CN | 104434263 A | 3/2015 |
| CN | 105188604 A | 12/2015 |
| CN | 107072770 A | 8/2017 |
| CN | 108852555 A | 11/2018 |
| EP | 1179321 A2 | 2/2002 |
| JP | H09276414 A | 10/1997 |
| JP | 2002542879 A | 12/2002 |
| JP | 2003508114 A | 3/2003 |
| JP | 2007527264 A | 9/2007 |
| JP | 2010517622 A | 5/2010 |
| JP | 4712707 B2 | 6/2011 |
| WO | WO-9601591 A1 | 1/1996 |
| WO | WO00/07656 A1 | 2/2000 |
| WO | WO00/27292 A1 | 5/2000 |
| WO | WO03/043538 A2 | 5/2003 |
| WO | WO03/047648 A2 | 6/2003 |
| WO | WO03/073961 A1 | 9/2003 |
| WO | WO03/094791 A2 | 11/2003 |
| WO | WO2004/021922 A2 | 3/2004 |
| WO | WO-2004019817 A1 | 3/2004 |
| WO | WO2006/138391 A2 | 12/2006 |
| WO | WO2008/066881 A1 | 6/2008 |
| WO | WO2009/038799 A1 | 3/2009 |
| WO | WO2013/103979 A1 | 7/2013 |
| WO | WO2015/185870 A1 | 12/2015 |
| WO | WO2016/040923 A2 | 3/2016 |
| WO | WO2017/074530 A1 | 5/2017 |
| WO | WO-2017116828 | 7/2017 |

OTHER PUBLICATIONS

International search report and written opinion dated May 5, 2017 for PCT Application No. PCT/US2016/067686.
Notice of allowance dated Jan. 17, 2020 for U.S. Appl. No. 15/137,924.
Office action dated Jun. 6, 2019 for U.S. Appl. No. 15/137,924.
Office action dated Jun. 30, 2021 for U.S. Appl. No. 16/808,859.
Office action dated Sep. 26, 2019 for U.S. Appl. No. 15/137,924.
Office action dated Oct. 26, 2018 for U.S. Appl. No. 15/137,924.
U.S. Appl. No. 16/808,859 Notice of Allowance dated Apr. 6, 2022.
U.S. Appl. No. 16/808,859 Office Action dated Feb. 24, 2022.
Russell et al.; U.S. Appl. No. 18/658,983 entitled "Integrated embolic protection devices," filed May 8, 2024.

* cited by examiner

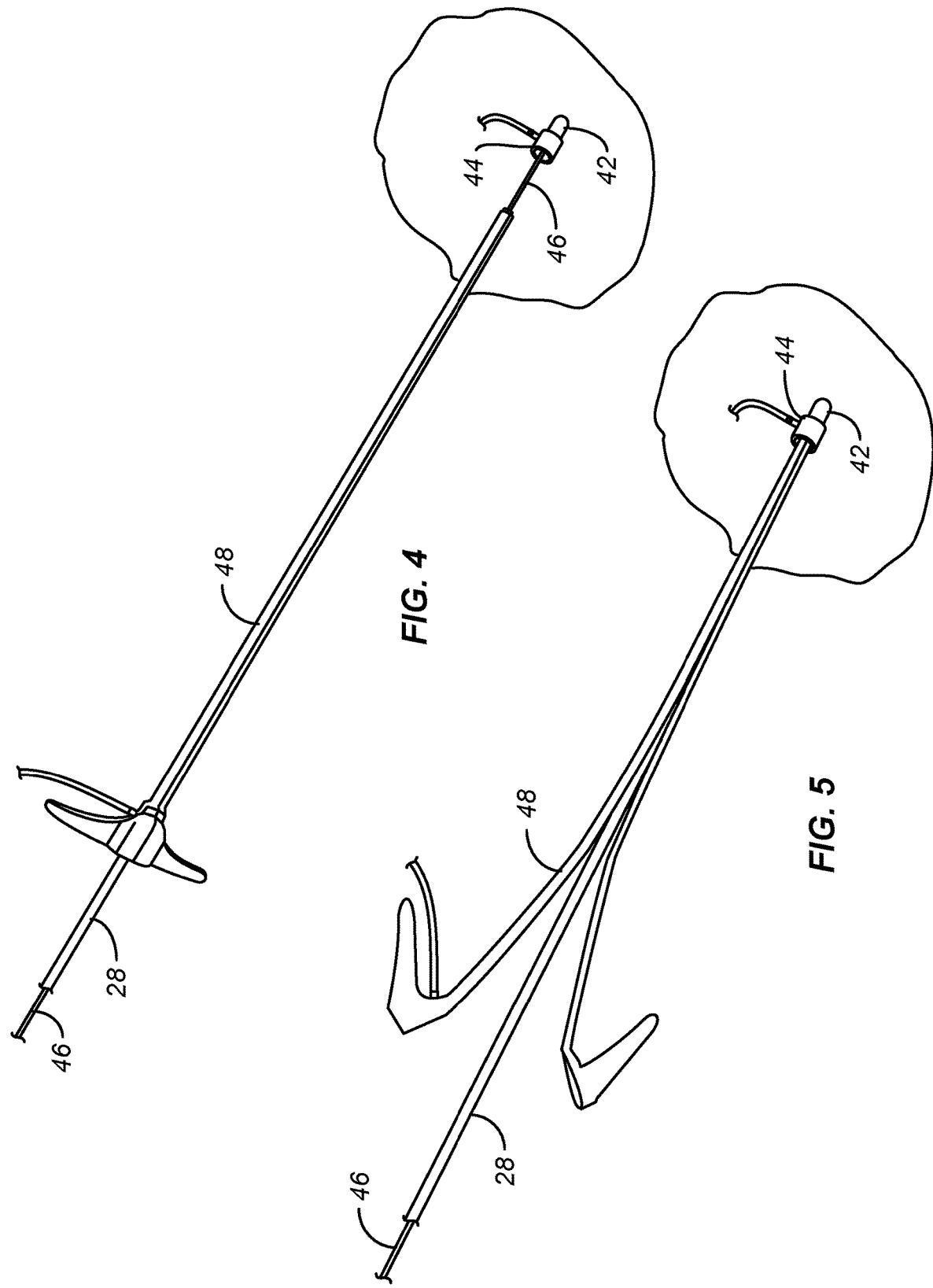

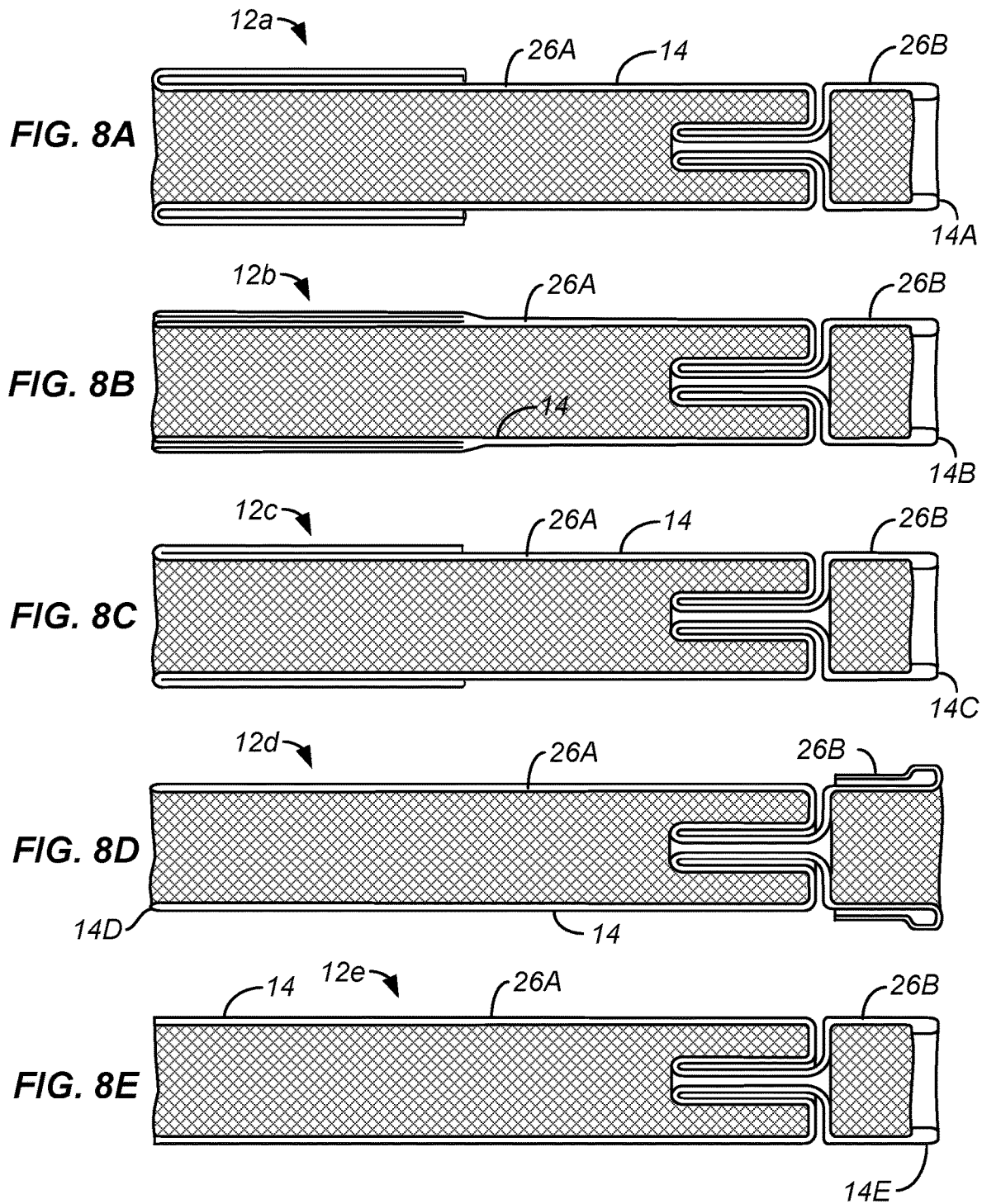

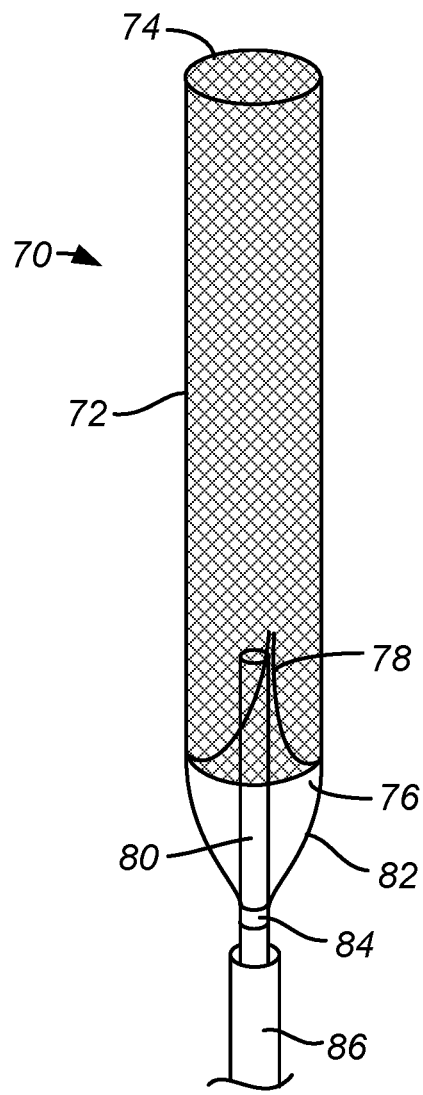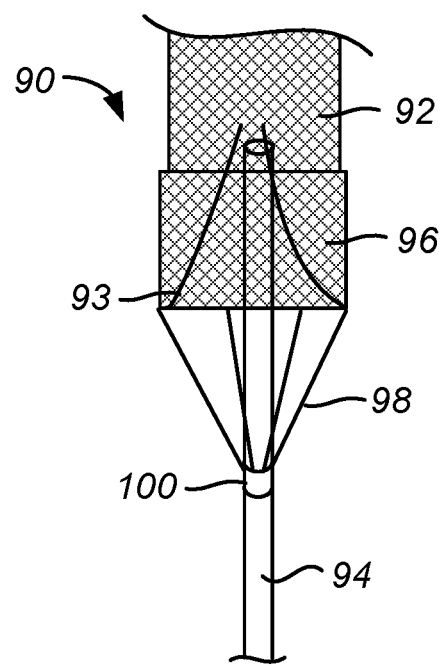
FIG. 9
FIG. 10

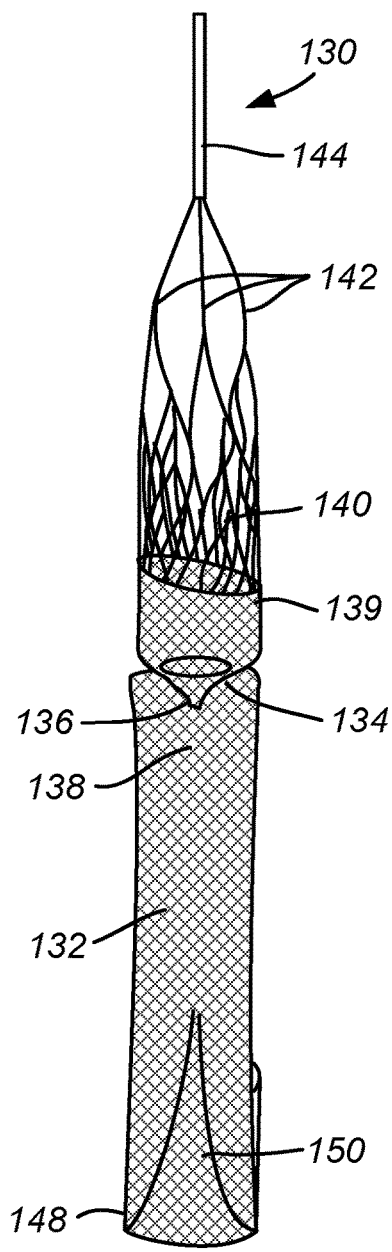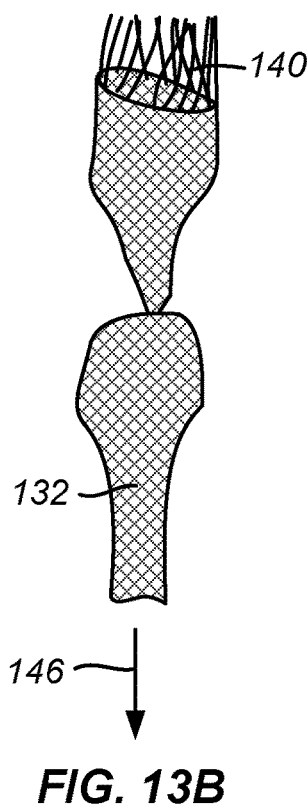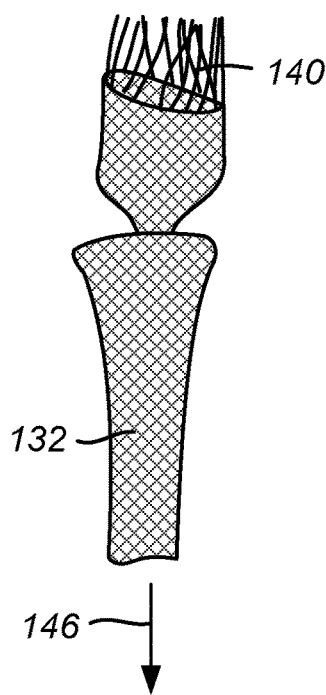
FIG. 13A
FIG. 13B
FIG. 13C

MULTI-ACCESS INTRAPROCEDURAL EMBOLIC PROTECTION DEVICE

CROSS-REFERENCE TO RELATED APPLICATION

This application is a continuation of Ser. No. 17/858,637, filed Jul. 6, 2022, which is a continuation of U.S. patent application Ser. No. 16/808,859, filed Mar. 4, 2020, now U.S. Pat. No. 11,399,927, which is a divisional of U.S. patent application Ser. No. 15/137,924, filed Apr. 25, 2016, now U.S. patent application Ser. No. 10,617,509, which claims the benefit of U.S. Provisional Application Nos. 62/272,643, filed Dec. 29, 2015; 62/294,018, filed Feb. 11, 2016; and 62/297,053, filed Feb. 18, 2016, the full disclosures of which are incorporated herein by reference.

The disclosure of this application is also related to the disclosures of commonly owned, U.S. patent application Ser. No. 14/537,814, filed Nov. 10, 2014 and U.S. patent application Ser. No. 13/735,864, filed Jan. 7, 2013, the full disclosures of which are incorporated herein by reference. Priority is not being claimed from the applications listed in this paragraph.

BACKGROUND OF THE INVENTION

1. Field of the Invention

The present invention relates generally to medical devices and methods and more particularly to apparatus and methods for providing embolic protection to a patient's aortic arch vessels during cardiac surgery and interventional cardiology procedures.

Cerebral embolism is a known complication of cardiac surgery, cardiopulmonary bypass, and catheter-based interventional cardiology and electrophysiology procedures. Embolic particles, including thrombus, atheroma, and lipids, may become dislodged by surgical or catheter manipulations, enter the bloodstream, and "embolize" to the brain or other vital organs downstream. Cerebral embolism can lead to neuropsychological deficits, stroke, and even death. Other organs downstream of an embolic release can also be damaged, resulting in diminished function or organ failure.

Of particular interest to the present invention, a number of procedures are performed on aortic valves using catheters advanced over the patient's aortic arch. Valvuloplasty procedures have been performed for many years and use high pressure balloons advanced over the aortic arch to disrupt calcifications on the aortic valve. Such procedures present a significant risk of emboli release to the cerebral arteries. More recently, percutaneous aortic valve replacement (PAVR) procedures, also known as transcatheter aortic valve implantation (TAVI) procedures or transcatheter aortic valve replacement (TAVR) procedures, have been approved, and their use has become widespread. While offering many patient benefits, they also present a significant risk of emboli release, particularly when performed transvascularly with catheters introduced over the aortic arch.

The prevention of embolism in these and other procedures would benefit patients and improve the outcome of many surgical procedures. Given that potential emboli are often dislodged during catheter-based procedures that involve more than one access site and more than one procedural device, it would be advantageous to deploy an embolic protection system that provides multiple access paths through or beyond the protection device to perform diagnostic and interventional procedures with multiple catheters.

It would be further advantageous to integrate the embolic protection system on a sheath that is being used to perform the procedure, such as is used with an angiographic diagnostic catheter, a transcatheter valve delivery system, and an electrophysiology catheter.

U.S. Patent Publ. No. 2015/0066075, commonly assigned herewith, describes an introducer sheath, intended specifically for use in valvuloplasty and TAVR procedure, which addresses some of the shortcomings of prior embolic protection sheath access devices. The '075 sheath includes embolic protection elements and is suitable for advancing a contrast or other small catheter through the sheath and a second catheter through port formed in a filter. While a significant improvement over previous embolic protection access sheathes having features, particular designs of the '075 access can be challenging to deploy and retrieve, can lose small amounts of emboli, and can have a relatively large profile during deployment.

Therefore, it would be desirable to provide improved devices, systems, and methods for preventing embolism during cardiac and other procedures performed over the aortic arch. Such devices, systems, and methods should offer less complicated deployment protocols, should have a relatively low profile when being deployed, and should afford reliable and efficient emboli containment at all times during a procedure. At least some of these objectives will be met by the inventions described herein.

2. Description of the Background Art

U.S. Patent Publ. No. 2015/0066075 has been described above. Other filters and devices for preventing cerebral embolism are described in U.S. Patent Publ. Nos. 2013/0178891; 2010/0312268; 2006/0287668; 2005/0010246; 2005/0283186; 2004/0215167; and 2003/0100940; PCT Publ. WO/2004/019817; and U.S. Pat. Nos. 8,114,114; 7,232,453; 6,712,834; 6,537,297; 6,499,487; 6,371,935; 6,361,545; 6,258,120; 6,254,563; 6,245,012; 6,139,517; and 5,769,819.

SUMMARY OF THE INVENTION

The present invention provides methods, systems, and devices for collecting emboli and in particular for preventing the release of emboli into the cerebral vasculature during the performance of interventional procedures in a patient's aorta, including aortic valve replacement, aortic valve valvuloplasty, and the like, where there is a risk of emboli being released into the aortic side vessels, including the brachiocephalic artery, the left carotid artery, and the left subclavian artery. The present invention provides embolic protection devices, tubular filter bodies, and systems and methods for placement of the devices and filters through the descending aorta and over the aortic arch to inhibit emboli release into the aortic side branch vessels while allowing simultaneous access to the aortic valve by one, two, three or more interventional and/or diagnostic catheters being introduced from the descending aorta, typically by conventional unilateral or bilateral femoral artery access.

The embolic protection devices include a filter body and a deployment catheter body connected to the filter body. The filter body typically comprises a tubular porous mesh material and has an open upstream end to allow the entry of blood flow and emboli and an open downstream end to allow entry of at least one working catheter and usually two or more working catheters simultaneously. The deployment catheter body is directly or indirectly coupled to the open downstream end of the filter body, where upstream and downstream refer to the direction of blood flow, e.g. downstream is toward the descending aorta and away from the heart and aortic arch. At least one self-sealing port or passage is provided in an interior of the filter body, and the deployment catheter body typically has at least one lumen to provide at least one access route to an interior of the tubular filter body for introducing a diagnostic, interventional or other working catheter through the self-sealing port. Preferably, one or more additional working catheters may be introduced through the same self-sealing passage simultaneously or sequentially with a first catheter introduced through the sheath. Additional self-sealing or other catheter-access ports could be included to provide other, parallel access routes through the filter body but are not usually necessary as the self-sealing passage will typically have a diameter which is sufficiently expandable to allow the simultaneous passage of two or more catheters while being able to close to block emboli release when no catheter is present. Other axially aligned self-sealing catheter-access ports could also be included to provide additional emboli capture chambers within the filter body.

In a first specific aspect of the present invention, an embolic protection device comprises a filter body formed from a tubular porous mesh material and having an open upstream end and an open downstream end. A self-sealing port is spaced inwardly from each of the ends, and the self-sealing port includes an expandable opening configured to conform to at least one working catheter passing therethrough. A radially collapsible support is coupled to a periphery of the downstream end of the filter body, and a catheter body having a distal end is coupled to the radially collapsible support, where distal refers to a direction on the device away from the operator, i.e., further away from the portion of the device that is outside the body. Similarly, the term proximal refers to a direction of the device closer to the operator, i.e., nearer to the portion of the device that is outside the body. A delivery sheath has a lumen configured to receive and radially constrain the filter body such that the catheter body may be distally advanced relative to the delivery sheath to release the filter body from constraint and to allow the filter body to radially expand with the support circumscribing the downstream end of the filter body. In this way, the catheter body may be distally advanced and proximally retracted relative to the delivery sheath to move the assembly of the support and filter body out of and into the lumen of the delivery sheath. In particular, when advanced out of the delivery sheath, the support will open to assist in deployment of the downstream end of the filter body and, when retracted back into the delivery sheath, the support will close to collapse the downstream end of the filter body prior to the filter body being drawn into the lumen.

In particular embodiments, the filter body has an open cylindrical chamber disposed between a downstream end of the port and the downstream end of the filter body. The port may comprise a wall portion up the tubular porous mesh material, where the wall portion folds, inverts, or otherwise deflects radially inwardly as other wall portions expand when released from radial constraint from the delivery sheath. In still other particular embodiments, the wall portion inverts to form a port having a conical opening or base on a downstream side. For example, the inverted wall portion of the tubular porous mesh material may have a resiliently closed sleeve portion extending in an upstream direction from an apex of the conical opening or base which defines the expandable opening of the port.

In still further particular embodiments, the radially collapsible support may comprise a loop secured around the periphery of the downstream end of the filter body. The loop may be connected to a tether which passes through a deployment lumen in the catheter body. The loop may be configured as a lasso to allow the tether to draw the open end of the filter body closed prior to drawing the filter body into the lumen of the delivery sheath. Alternatively, the radially collapsible support may comprise a scaffold having an open end coupled to the periphery of the downstream end of the filter body and a constricted end coupled to the distal end of the catheter body.

In still other particular embodiments of the present invention, the catheter body will include a lumen for receiving at least one working catheter so that the working catheter may be advanced through the lumen and into the open downstream end of the filter body and then through the port. The catheter body may further include at least one additional lumen for receiving a tether attached to the radially collapsible support. Additional lumens may also be provided for other purposes.

In a second specific aspect of the present invention, a luminal emboli capture device comprises a filter body formed from a tubular porous mesh material and having an open upstream end, an open downstream end, and at least a first port spaced inwardly from each of the ends. The port comprises an expandable opening configured to conform to at least one working catheter passing therethrough, and the filter body will have at least an open cylindrical chamber at its downstream end and an open cylindrical chamber at its upstream end, where the port is disposed therebetween. The emboli capture device may further comprise a catheter body having a distal end coupled to the downstream end of the filter body.

In specific embodiments, the porous mesh material comprises a fabric of knitted, braided, woven, or nonwoven fibers, filaments, or wires having a pore size chosen to prevent emboli over a predetermined size from passing therethrough. In many embodiments, the fabric will be double-walled over at least a portion of the tubular mesh, and the porous mesh material may be made of a resilient metal, a polymer material, a malleable material, a plastically deformable material, a shape-memory material, or combinations thereof. In further specific cases, the porous mesh material may have an anti-thrombogenic coating on its surface, and the pore size will typically be in the range from about 1 mm to about 0.1 mm. An exemplary porous mesh material comprises a double layer braid formed from 288 individual wires, including a combination of 276 Nitinol® (nickel-titanium alloy) wires and 12 tantalum wires, each wire being 0.002 inch in diameter, formed to a final double-layer mesh diameter of between 20 mm and 40 mm.

In further particular embodiments, the at least first port is formed from or comprises a wall portion of the tubular porous mesh material. The wall portion is formed or shaped, e.g. being thermally shaped and set, so that the port folds or closes radially inwardly as other wall portions expand when released from constraint. The wall portion will typically be pre-shaped to invert to form a port with a conical opening on a downstream side, and, typically, a closed sleeve portion extending in an upstream direction from an apex of the conical opening which defines the expandable opening of the port. In alternative embodiments, the port may be defined by a wall portion of the tubular porous mesh which is constricted, pinched, or otherwise closed radially inwardly but will open in response to the passage of the working catheter(s) therethrough. In a particular embodiment, in additional to the upstream and downstream chambers, the filter body may have one or more open "central" cylindrical chambers between a downstream end of the first or other port and an upstream end of the second or other port.

In a third specific aspect of the present invention, a clot retrieval system comprises an embolic protection device as just described in combination with a clot retrieval working catheter having a clot capture distal end, where the clot retrieval working catheter is configured to draw retrieved clot in a downstream direction through an open upstream end on the filter body into a central chamber.

In a fourth specific aspect, the present invention provides a method for advancing a working catheter into and/or over a patient's aortic arch. A cylindrical filter body formed at least partly from a porous mesh is provided. The cylindrical filter body defines a collection chamber for emboli and has an open upstream end, an open downstream end, a self-sealing port spaced inwardly from each of the ends, and a radially collapsible support coupled to a periphery of the downstream end of the filter body. A deployment catheter which carries and constrains the cylindrical filter body is advanced to a downstream side of the aortic arch while the filter body remains in its radially constrained configuration, typically with a previously placed delivery sheath. The cylindrical filter body is radially expanded so that a wall of the porous mesh covers the patient's aortic side or branch vessels and the open upstream end of the filter body faces the patient's heart. Blood flows into an interior of the filter body through the open upstream end, and emboli collect in the collection chamber. As the filter body is deployed, the support radially expands to hold the downstream end of the filter body open, and blood flowing through the porous mesh of the filter body and into the aortic side vessels is substantially emboli free. After the filter body is deployed, a first working catheter can be advanced through the open downstream end of the filter body and through the self-sealing port and toward the heart. Optionally, a second working catheter may be advanced through the open downstream end of the filter body and through the self-sealing port toward the heart, either simultaneously or sequentially with placement of the first working catheter.

In particular embodiments, a first diagnostic or interventional procedure may be performed with the first working catheter and a second diagnostic or interventional procedure may be performed with the second catheter. It will be appreciated that third, fourth, and additional working catheters may also be introduced and advanced either simultaneously or sequentially with other working catheters.

The first working catheter is typically introduced through a lumen in the deployment catheter, and the second working catheter may be introduced in parallel to the deployment catheter. In this way, the delivery profile of the deployment catheter can be minimized. In one example, a first working catheter will be used to introduce contrast media to an interventional site while a second working catheter will perform an interventional procedure at that site. More specifically, the interventional procedure may comprise delivery of a prosthetic aortic valve, performance of valvuloplasty, or the like.

In still further particular embodiments, the deployment catheter is advanced while present in a delivery sheath which radially constrains the cylindrical filter body. Radially expanding the cylindrical filter body may comprise proximally retracting the delivery sheath relative to the deployment catheter. Typically, the radially expanded filter body is retrieved by retracting the deployment catheter to collapse the radially collapsible support to close the open downstream end of the filter and draw the closed downstream end of the filter body into the delivery sheath. More specifically, retracting the deployment catheter to collapse the radially collapsible support may comprise retracting a tether present in the lumen of the deployment catheter to first collapse the radially collapsible support to close the downstream end of the filter body and then to retract the deployment catheter to draw the closed downstream end of the filter body into the delivery sheath.

In still further embodiments, the filter may contain one or more support structures or wires that provide longitudinal stiffness to the device to prevent compression or movement of the filter during the procedure. Such wires or structures may extend the full length of the device or only for a portion of its length and such wires or structures shall be either fixedly or slidably attached to the access sheath.

BRIEF DESCRIPTION OF THE DRAWINGS

FIGS. 4 and 5 illustrate use of a peel-away catheter for introducing the filter body of the embolic protection device of FIG. 1 into a port of a delivery sheath for advancement to an aortic arch in accordance with the principles of the methods of the present invention.

FIGS. 8A-8E illustrate a number of different folding patterns for a tubular porous mesh material in order to form filter bodies useful in the embodiments of the present invention.

FIG. 9 illustrates a second embodiment of an embolic protection device constructed in accordance with the principles of the present invention.

FIG. 10 illustrates a third embodiment of an embolic protection device constructed in accordance with the principles of the present invention.

FIGS. 13A-13C illustrate a fifth embodiment of an embolic protection device constructed in accordance with the principles of the present invention, and further show a stepwise formation of a self-sealing valve in a filter body of the device.

DETAILED DESCRIPTION OF THE INVENTION

Figure 1:
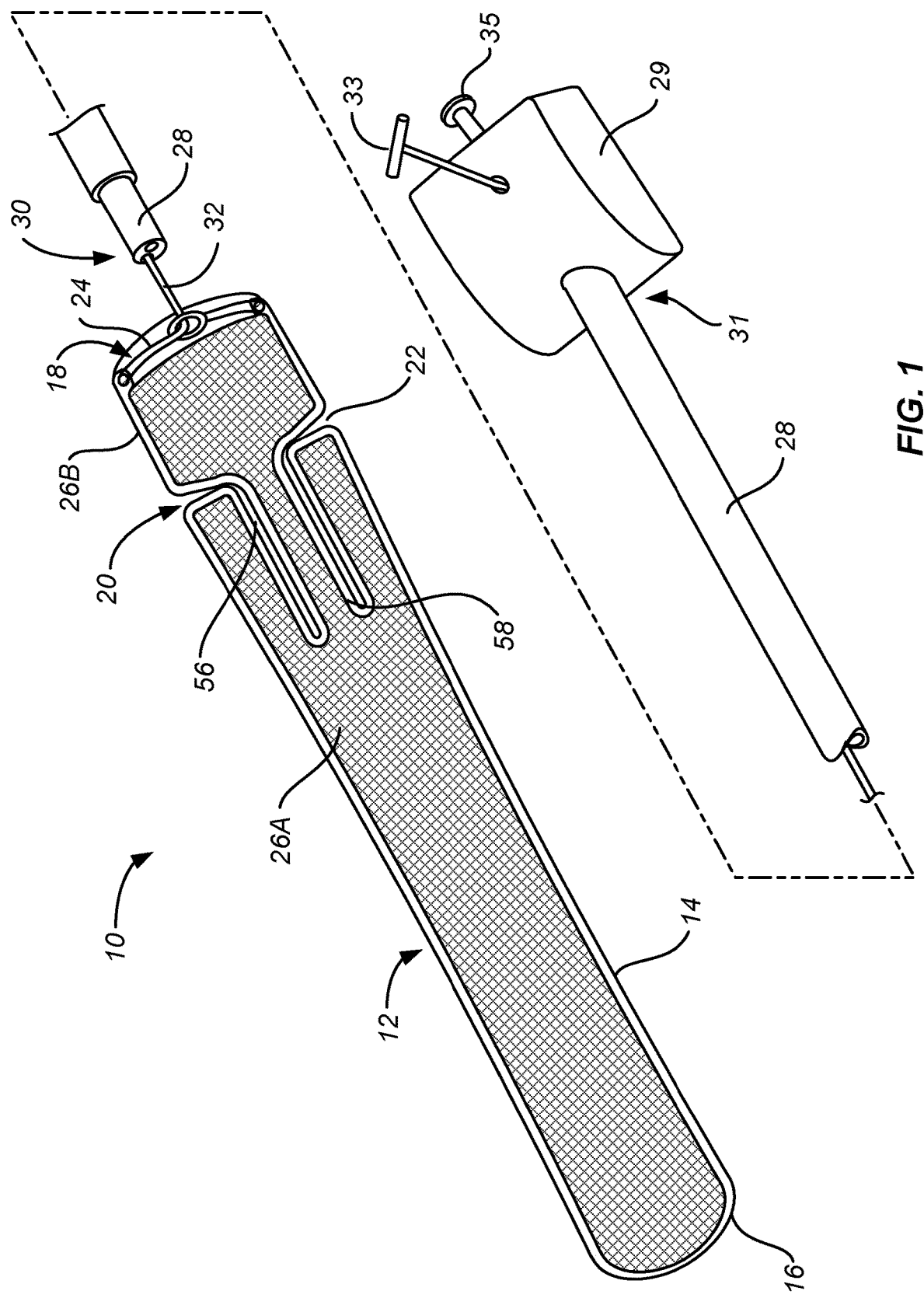
FIG. 1 is a partially exploded view of a first embodiment of an embolic protection device constructed in accordance with the principles of the present invention.
Figure 2:
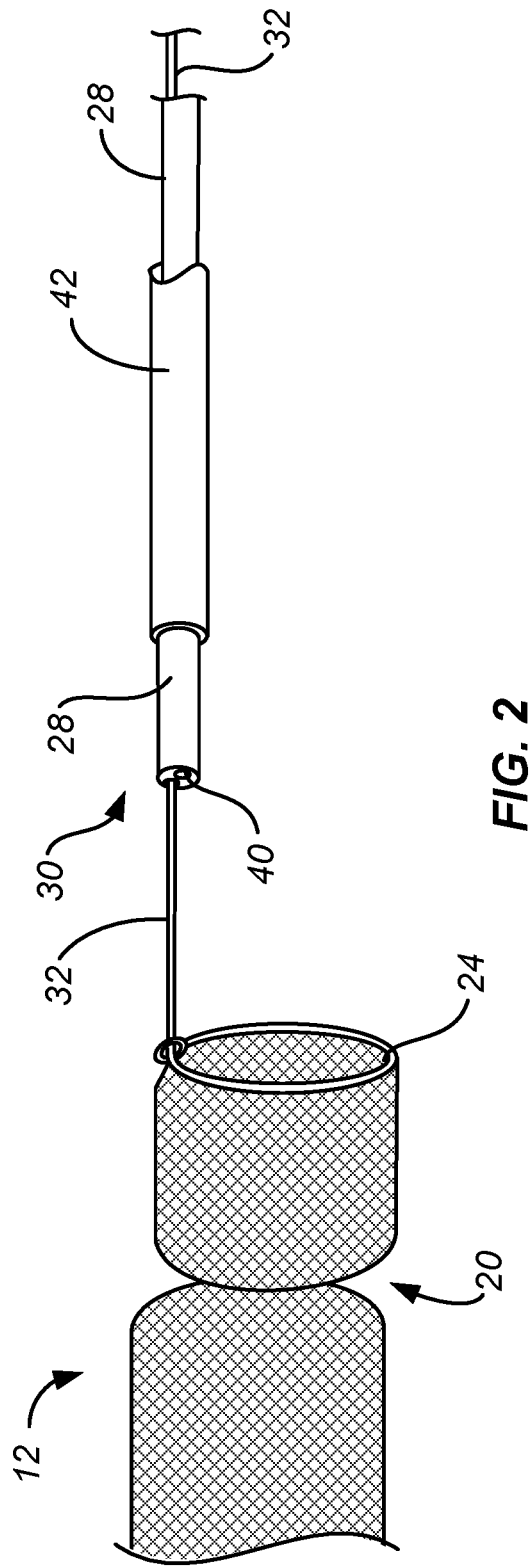
FIG. 2 is a detailed view of the connection between a filter body and a deployment catheter body of the embolic protection device of FIG. 1.
Figure 3:
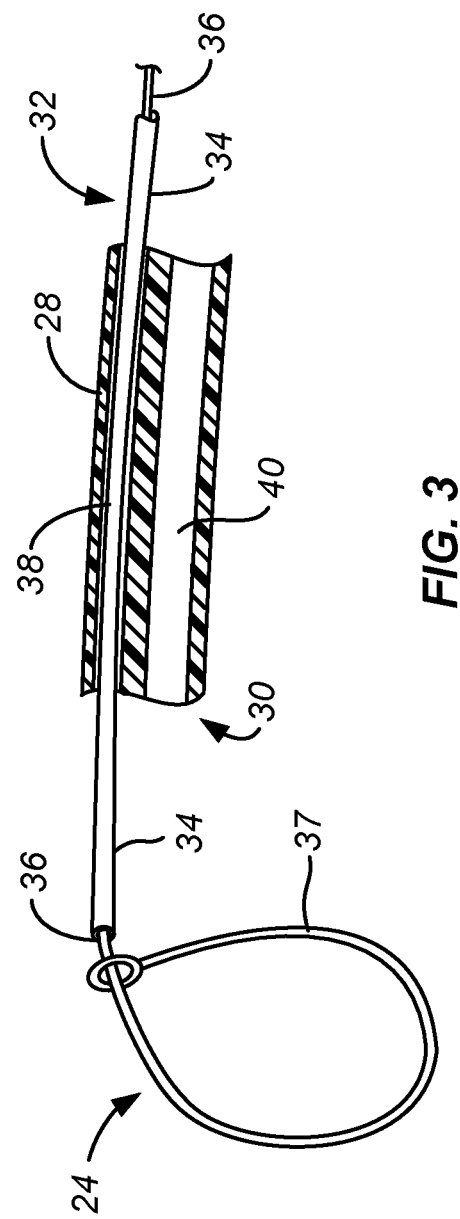
FIG. 3 is a detailed view shown in partial section of a tether structure which connects a downstream end of the filter body to an upstream or distal end of the catheter body of the embolic protection device of FIG. 1.

As shown in FIGS. 1-3, an embolic protection device 10 constructed in accordance with the principles of the present invention comprises a filter body 12 having an open upstream end 16 and an open downstream end 18. The filter body 12 is typically formed from a porous mesh material, more typically a tubular porous mesh material which is preformed to have a self-sealing port 20 with an expandable opening 22 located between the open upstream end 16 and the open downstream end 18, typically closer to the open downstream end as illustrated. Specific folding patterns for the filter body 12 are described below with reference to FIGS. 8A-8E, and several exemplary alternative folding patterns are described below in connection with FIGS. 15A-15C.

A radially expandable/collapsible support 24 is secured at the open downstream end 18 of the filter body 12, as best seen in FIG. 2. The radially collapsible support 24 may comprise a tube 34 (FIG. 3) having a pull wire 36 with a loop 37 formed at its distal end. The loop 37 is secured about the periphery of the open downstream end 18 of the filter body 12 so that it may act as a "lasso" or a "purse-string" component for opening and closing the open downstream end 18. In particular, by proximally retracting the pull wire 36 within the tube 34 (to the right in FIG. 3), the loop 37 may be closed. Conversely, by distally advancing the pull wire 36 relative to the tube 34, the loop 37 may be open. As described in more detail below, by axially advancing and retracting the tether structure 32, the filter body 12 may be positioned relative to a deployment catheter body 28.

The self-sealing port 20 of the filter body 12 divides the filter body into an upstream cylindrical chamber 26A and a downstream cylindrical chamber 26B. Each of the chambers 26A and 26B will be generally free from internal structure, and the self-sealing port 20 will act to divide the two chambers and, in particular, to prevent passage of emboli which may enter the upstream chamber 26A into or beyond the downstream chamber 26B. The downstream cylindrical chamber 26B acts to receive and facilitate introduction of working catheters into and through the self-sealing port 20 in order to perform interventional procedures upstream of the filter body 12 when the filter body is deployed in the aorta or other blood vessels.

The deployment catheter body 28 has a distal end 30 and at least a first lumen 38 for carrying the tether structure 32 and a second lumen 40 which serves as a working lumen for introducing interventional or working catheters therethrough, such as TAVR catheters for deploying prosthetic aortic valves as will be described in detail below.

A proximal or control hub 29 is coupled to a proximal end 31 of the deployment catheter body 28. A proximal end 33 of the tether structure 32 extends from the control hub 29 and allows a user to manipulate the tether structure, and including both axial retraction and advancement of the tether structure as well as opening and closing of the loop 37. The control hub 29 also has a port 35 which opens to the second lumen 40 in the catheter body 28 for allowing passage of guide wires, working catheters, and the like.

The filter body 12 will typically be self-expanding. By "self-expanding," it is meant that the filter body will be resilient and have a normally open or expanded configuration when free from radial and/or axial constraint. By either radially contracting or axially extending the filter body, the diameter or profile of the filter body will be reduced so that it can be intravascularly introduced to a working site in the patient's vasculature, typically over the aortic arch but optionally in other locations as well. Additionally, by radially collapsing and/or axially extending the filter body, the self-sealing port within the filter body will be unfolded and axially extended.

The self-sealing port 20 will be self-forming, typically having a conical base 56 and an extending sleeve 58, as shown in FIG. 1. The self-sealing port 20 will have at structure which is formed by folding and inverting the generally tubular structure of the filter body as the radius of the filter body increases and the length of the filter body axially shortens. The necessary fold lines will be pre-formed into the filter body, typically by heat treatment. In exemplary embodiments, the filter body will be formed as a Nitinol® (nickel-titanium alloy) thin wire mesh which will be formed to have the fold lines described in more detail with reference to FIGS. 8A-8E below. These pre-formed fold lines will allow the filter body to be axially elongated and radially collapsed to have a low profile during delivery, typically having a delivery diameter below 12 Fr (French), often below 10 Fr. Conversely, the filter body will typically open to an unconstrained width or diameter above 5 mm, often above 15 mm more often above 25 mm, and typically in the range from 25 mm to 40 mm. As will be described in more detail below, the filter body 12 will be introduced in its low profile configuration through a delivery sheath 42 which has been pre-placed in the patient's artery, typically through the femoral artery over the aortic arch. In order to advance the filter body into the delivery sheath 42, however, it is necessary to temporarily constrain the self-expanding filter body 12. This may be achieved using a peel-away sheath 48, as shown in FIGS. 4 and 5. The filter body 12 is axially elongated and radially collapsed and drawn into the lumen of the peel-away sheath 48, as shown in FIG. 4. The peel-away sheath covers the filter body 12 with the catheter body 28 extending from a proximal end of the peel-away sheath 48. The temporary assembly of the peel-away sheath and the catheter body 28 can be introduced over a guidewire structure 46 which has been pre-placed through a distal port 44 of the delivery sheath 42, as shown in FIG. 4, with the sheath then being advanced through the distal port 44, as shown in FIG. 5. Once the distal end of the filter body 12 has been introduced through the port 44 into the proximal end of the delivery sheath 42, the peel-away sheath may be removed as the filter body continues to be introduced into the delivery sheath 42. To facilitate delivery, each of the delivery sheath 42 and the peel-away sheath 48 may have ports to allow the introduction of fluids into their lumens.

Figure 6:
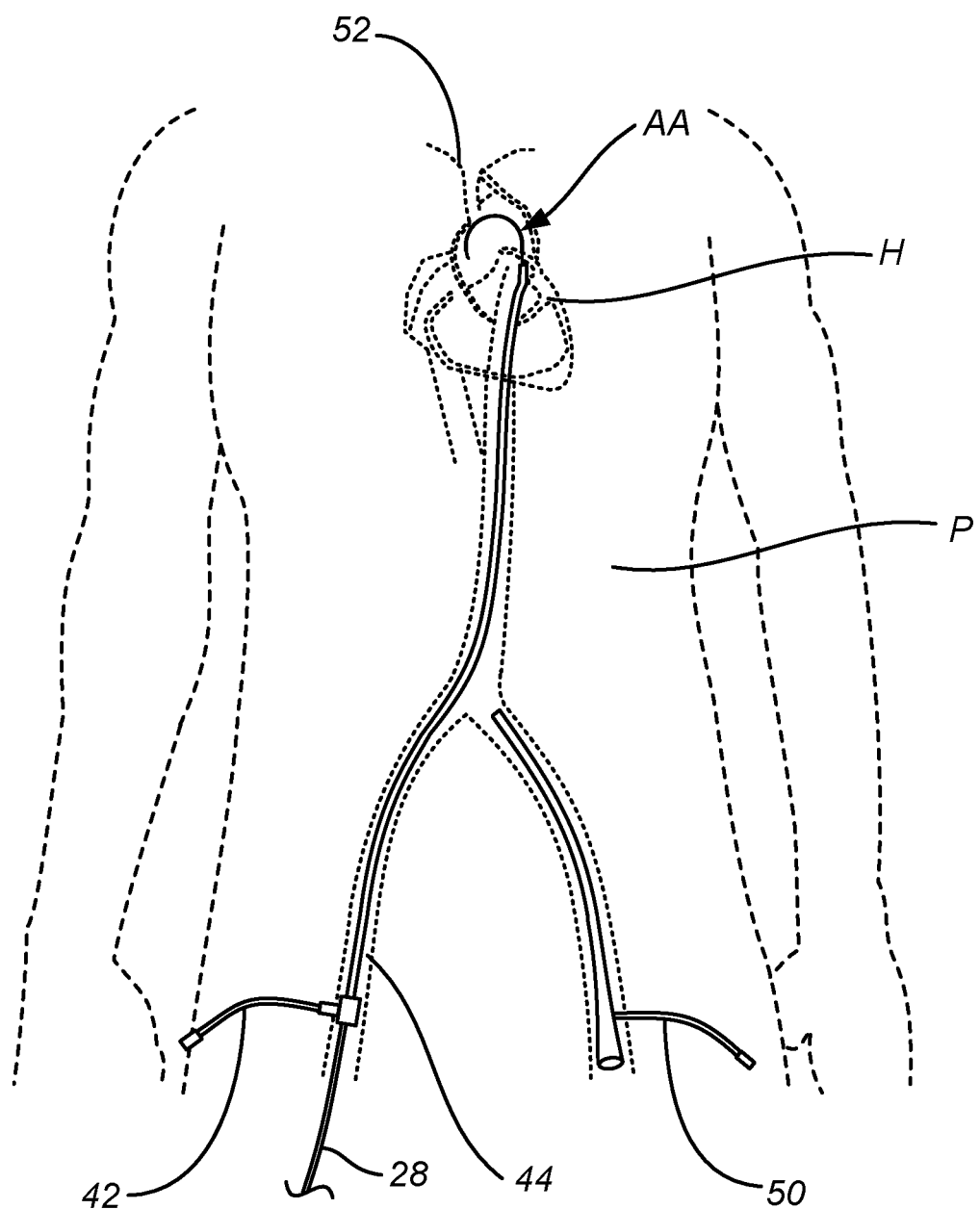
FIG. 6 illustrates the contralateral positioning of the delivery sheath for placement of the embolic protection device and a separate transcatheter aortic valve replacement (TAVR) catheter as would be used for placement of a prosthetic heart valve using the embolic protection device of the present invention.

As shown in FIG. 6, the delivery sheath 42 will be introduced through the patient's groin into a femoral artery and up and over the aortic arch in a conventional manner. A second sheath 50, typically for introducing a TAVR or other interventional or working catheter, will be positioned in the contralateral femoral artery for introducing the working catheter up the aorta and over the aortic arch AA in parallel to the delivery sheath 42. Such positioning will be intended for prosthetic valve placement or other interventional procedures on the patient's P heart H.

Figure 7A:
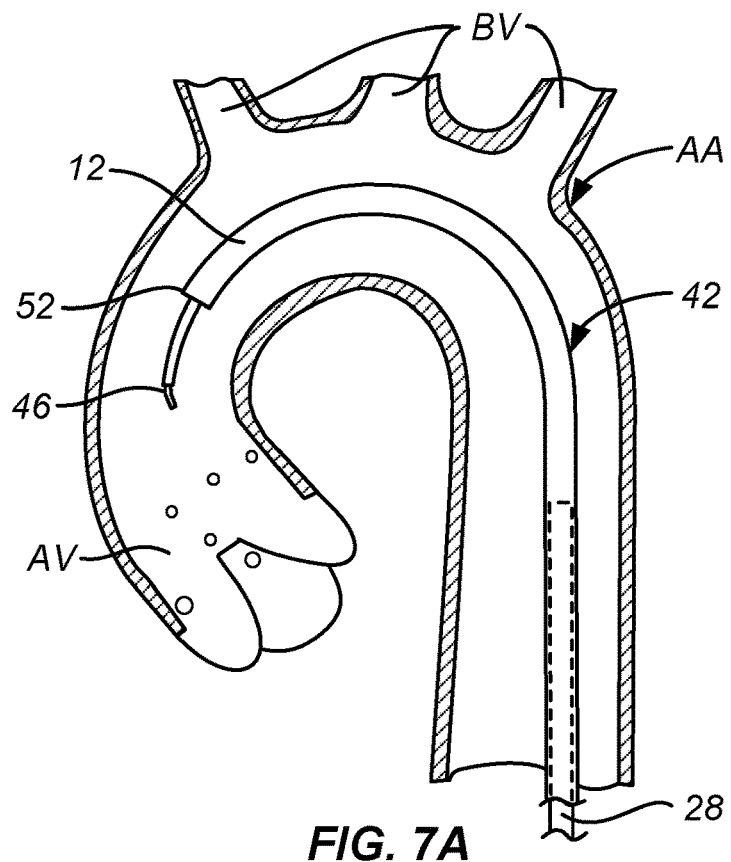
FIGS. 7A-7ZZ illustrate positioning of the embolic protection device of the present invention over a patient's aortic arch and delivery of a prosthetic aortic valve through the embolic protection device in accordance with the methods of the present invention.
Figure 7B:
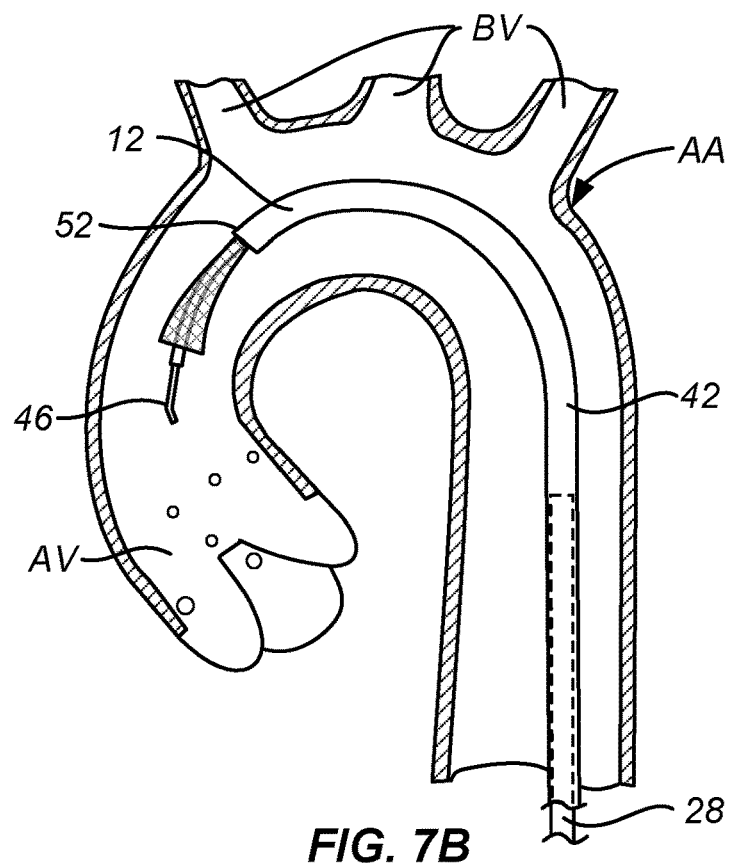
Figure 7C:
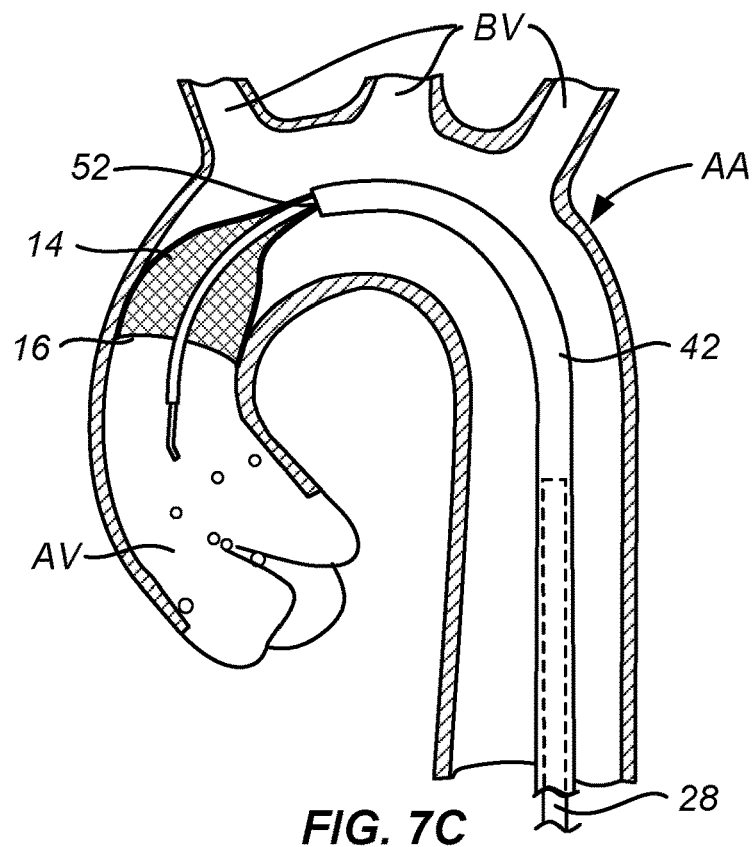
Figure 7D:
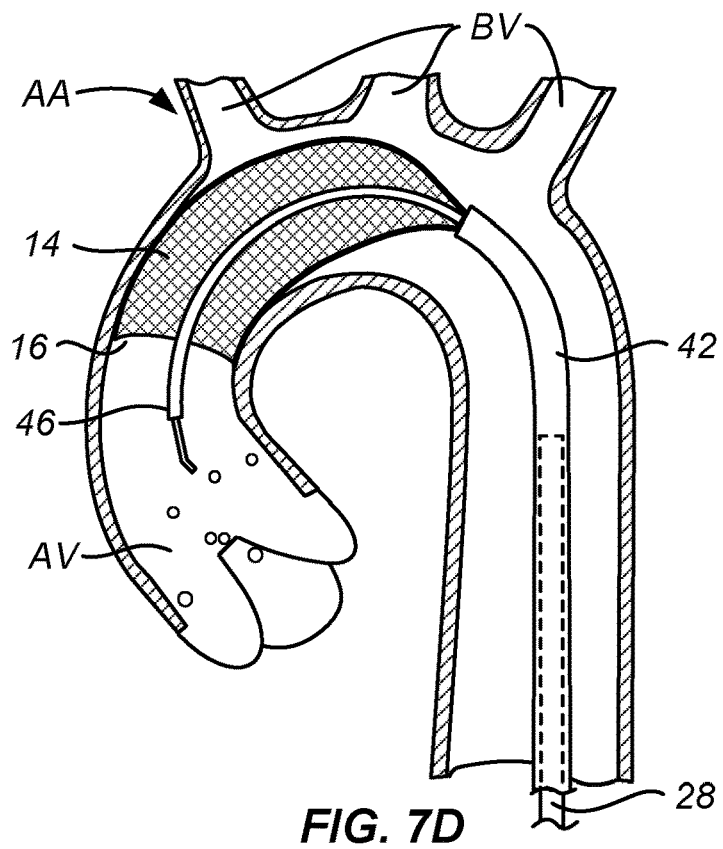
Figure 7E:
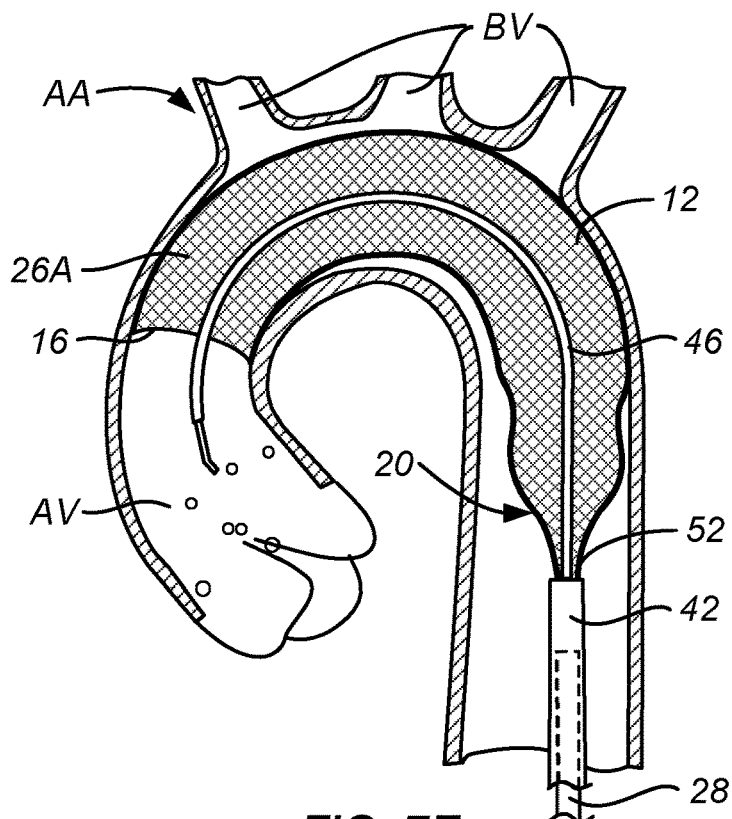
Figure 7F:
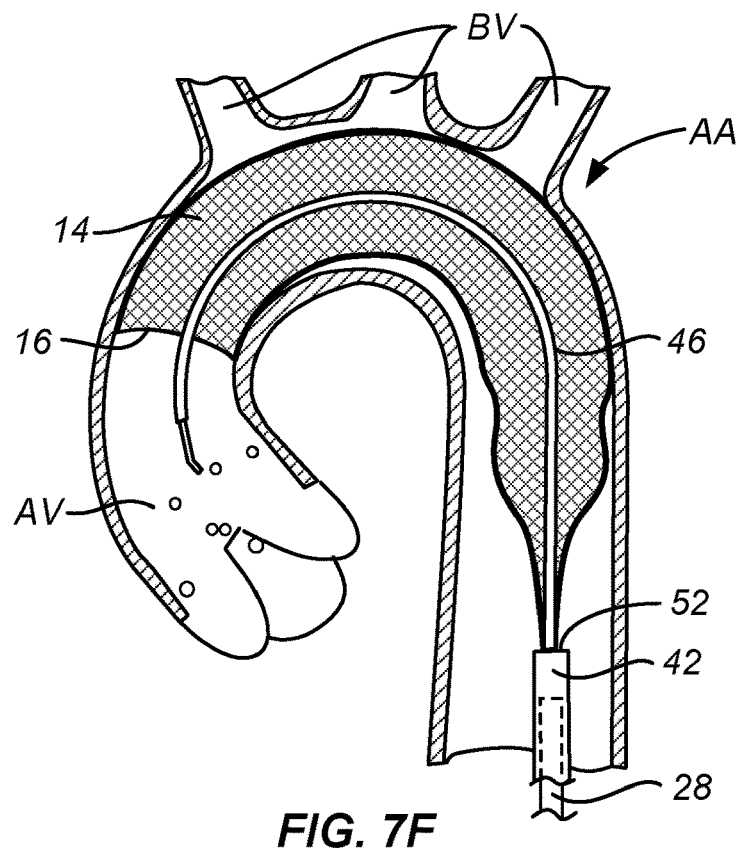
Figure 7G:
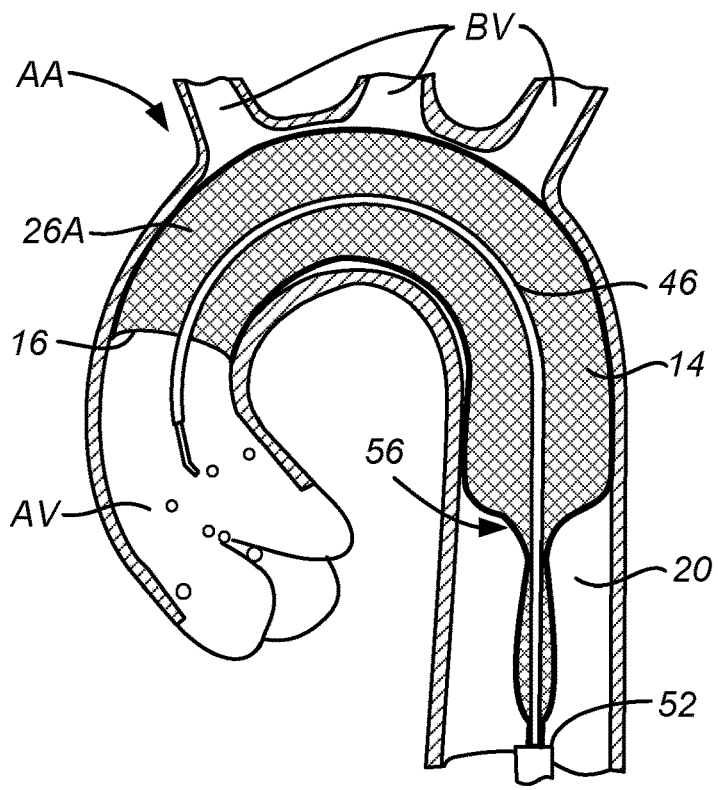
Figure 7H:
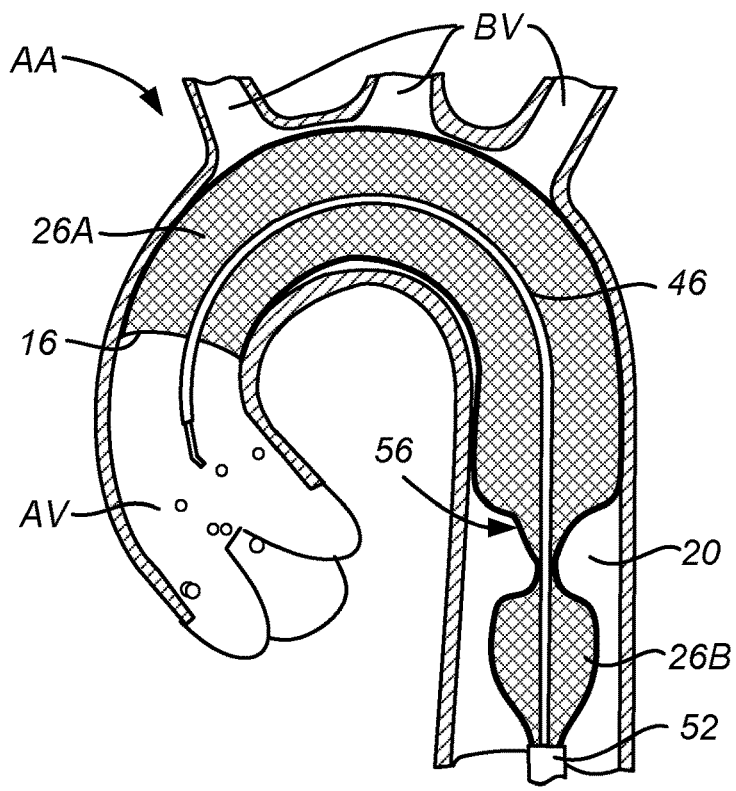
Figure 7I:
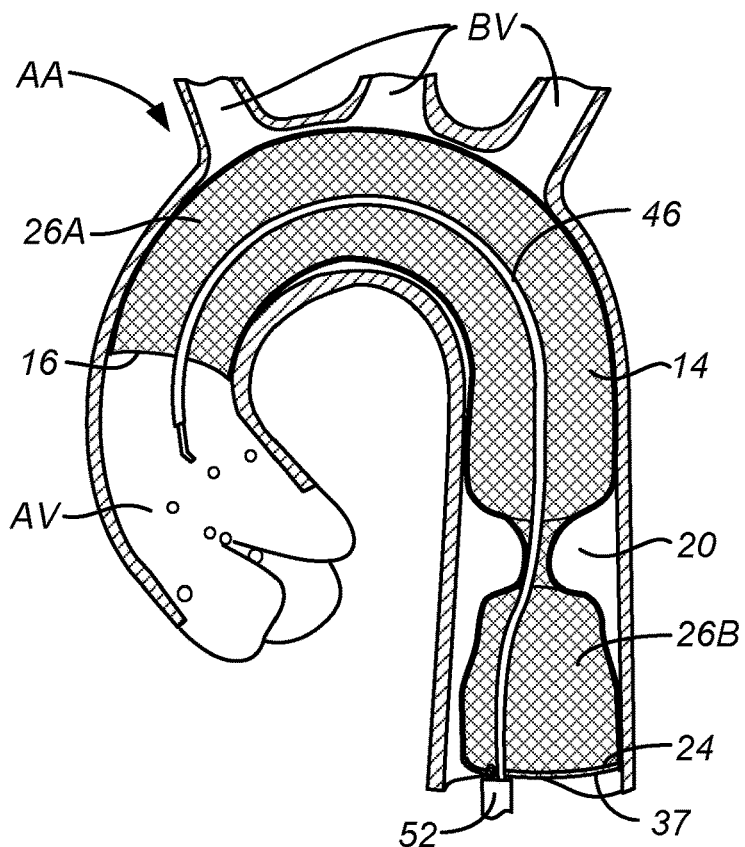
Figure 7J:
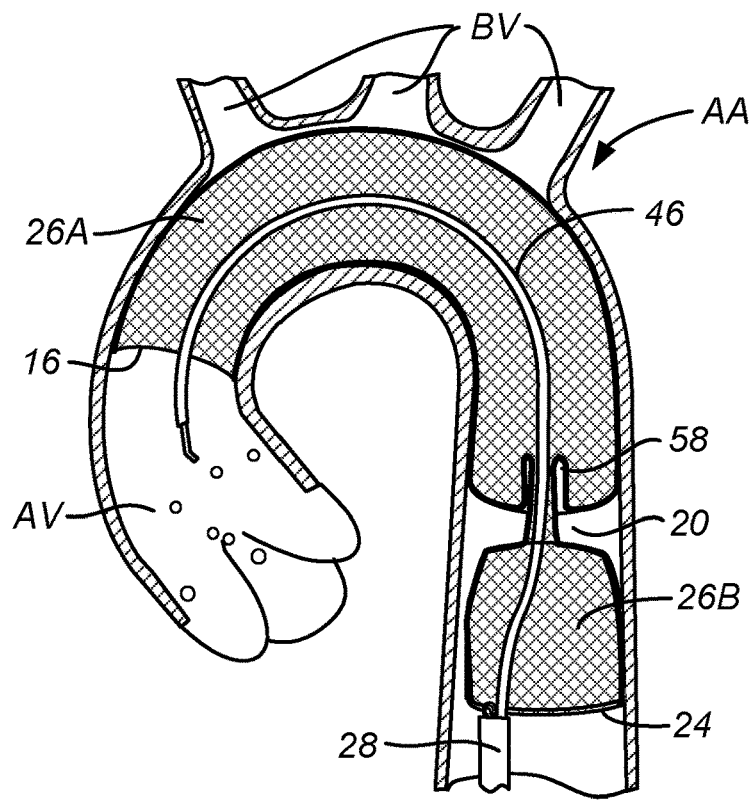
Figure 7K:
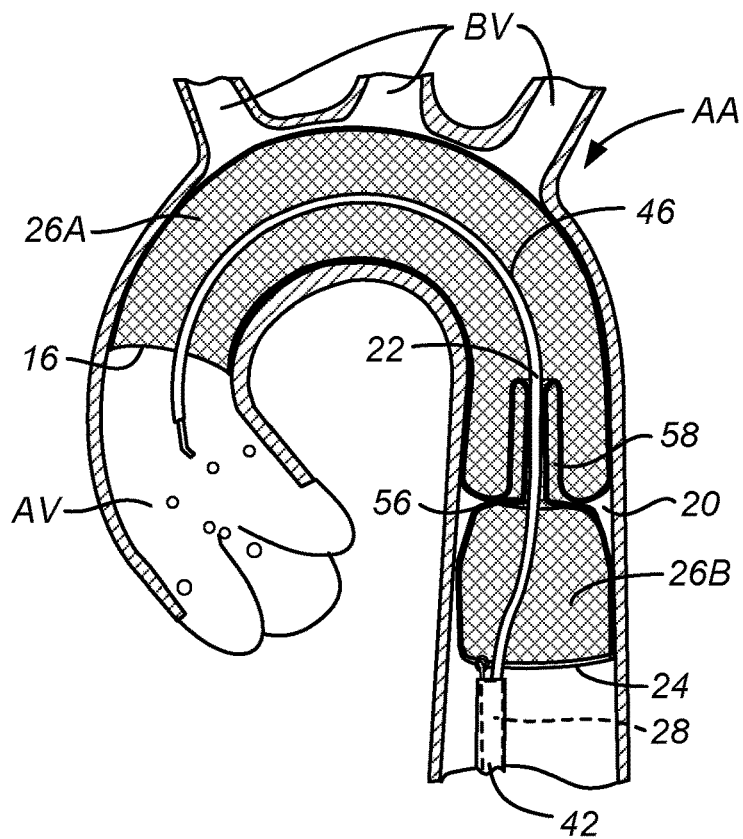
Figure 7L:
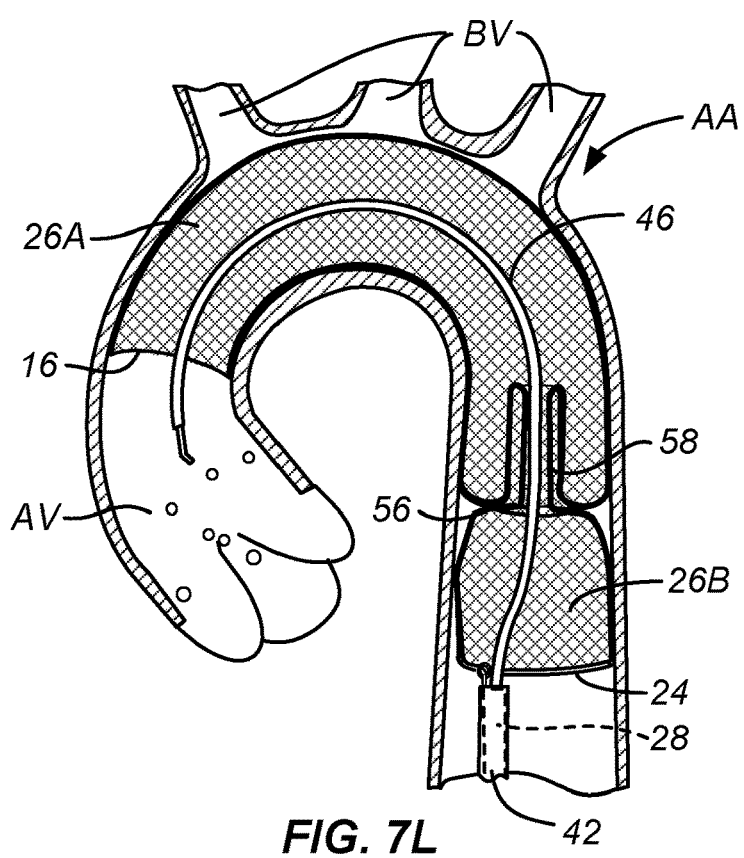
Figure 7M:
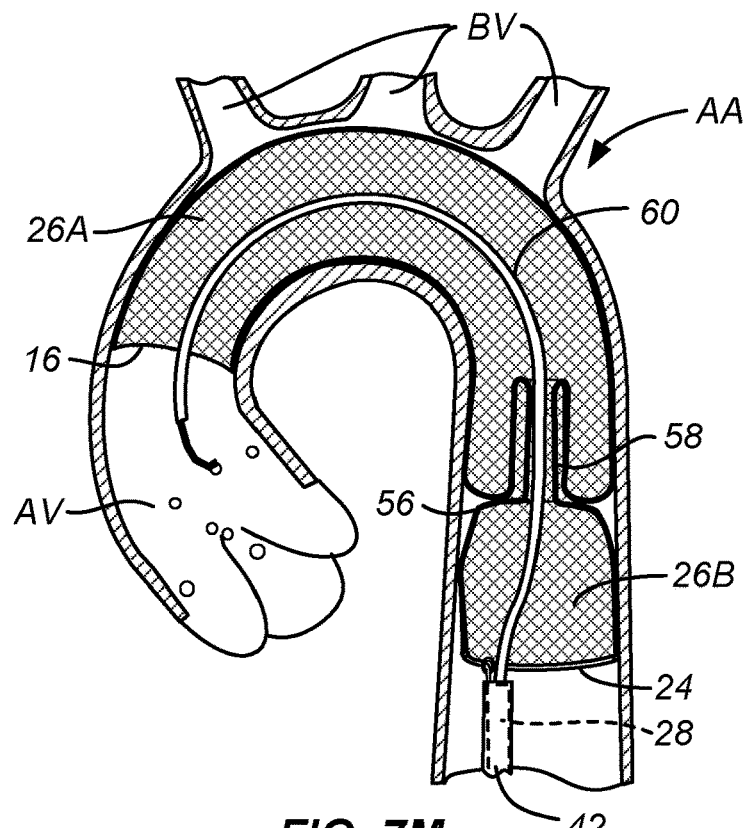
Figure 7N:
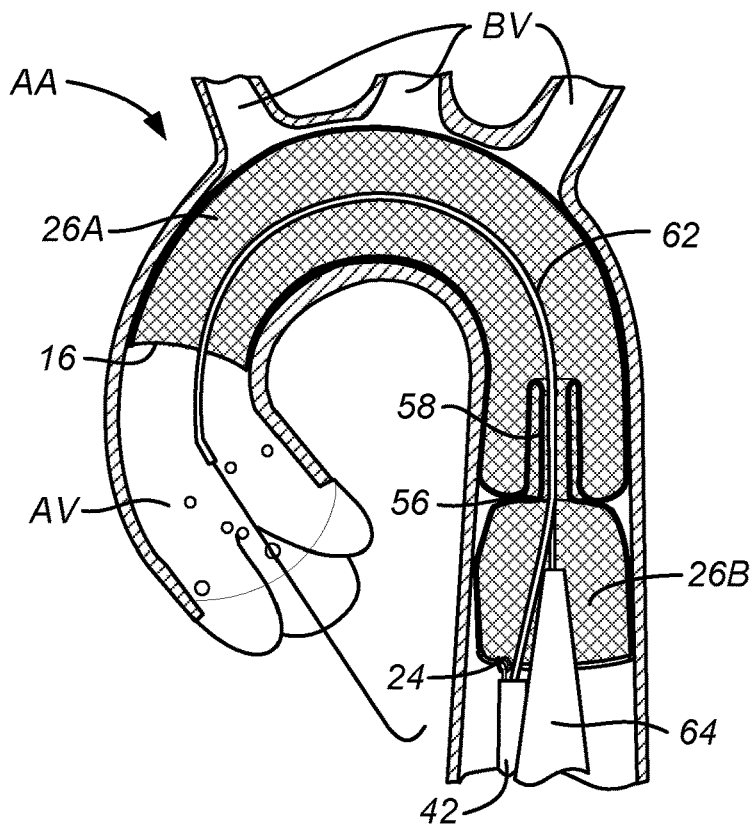
Figure 7O:
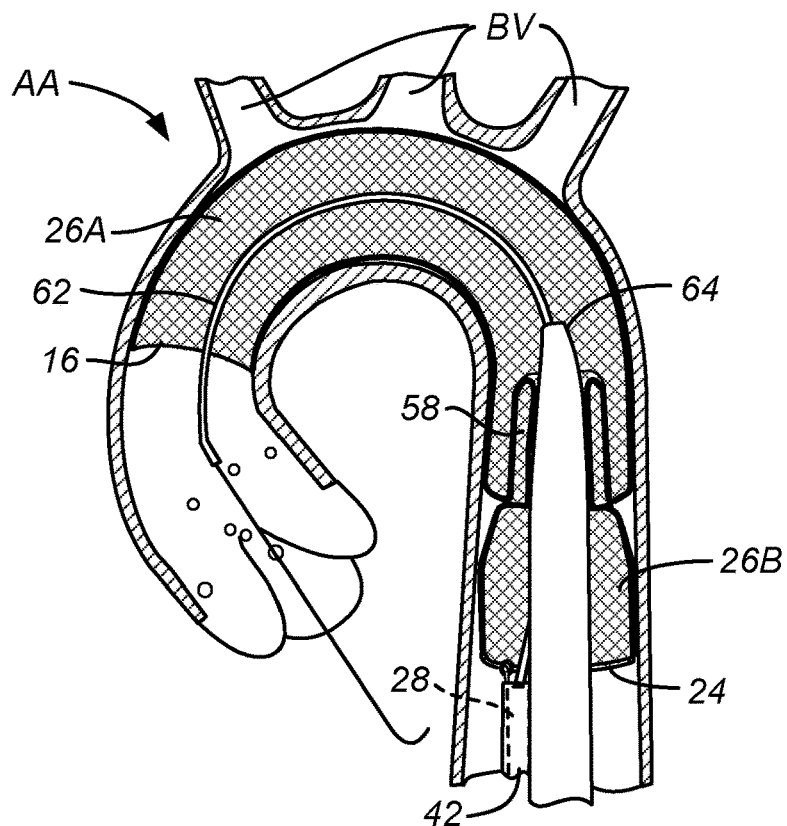
Figure 7P:
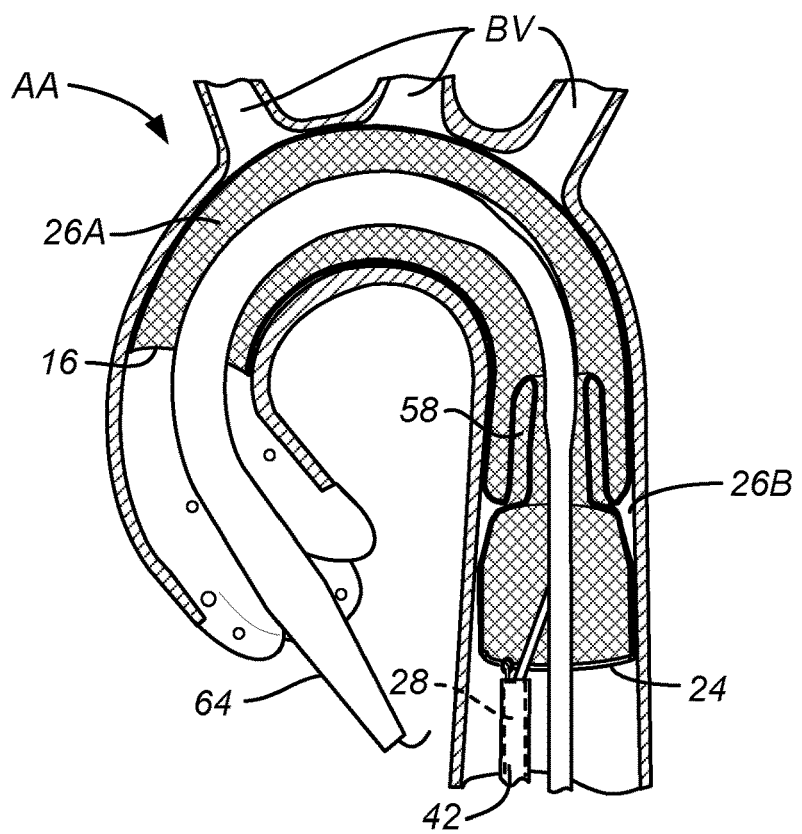
Figure 7Q:
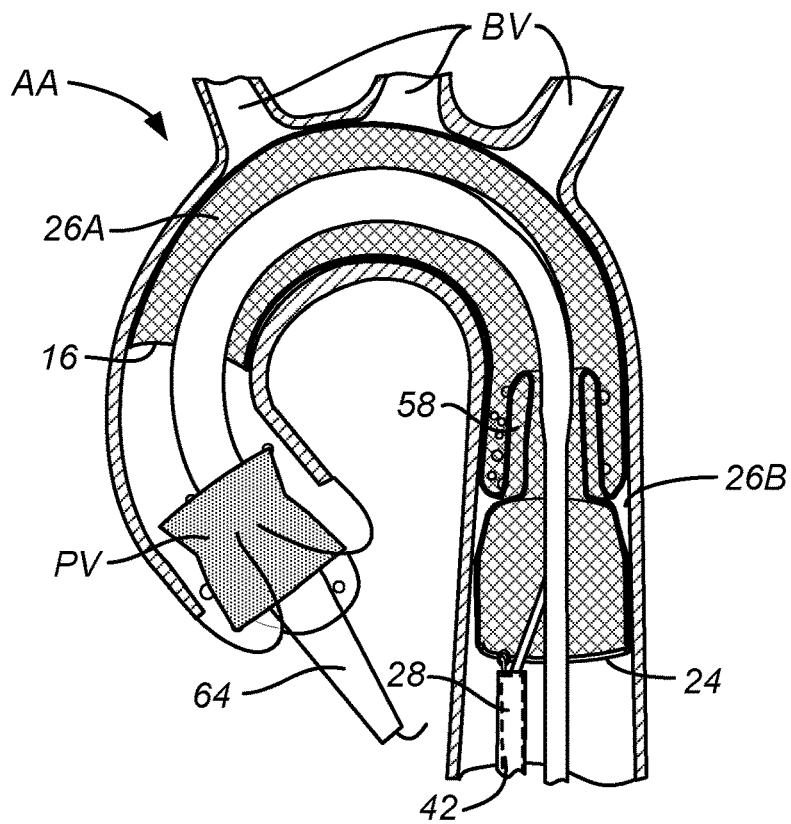
Figure 7R:
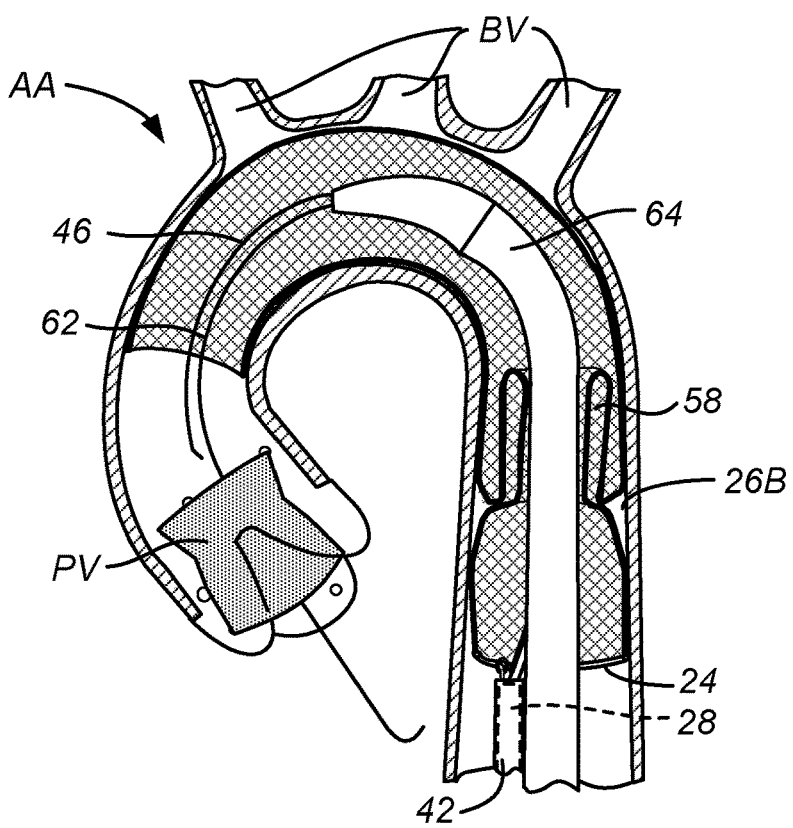
Figure 7S:
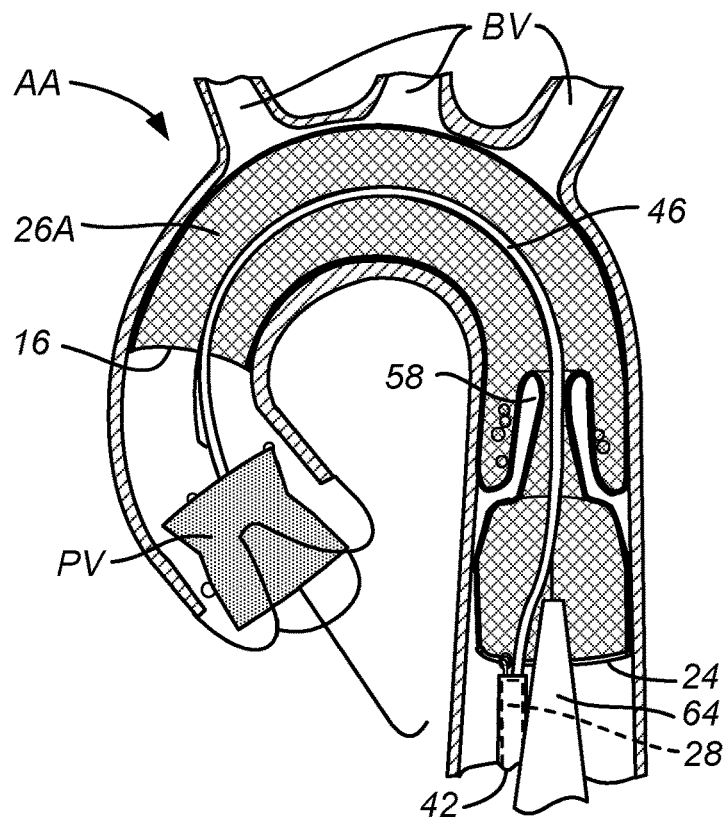
Figure 7T:
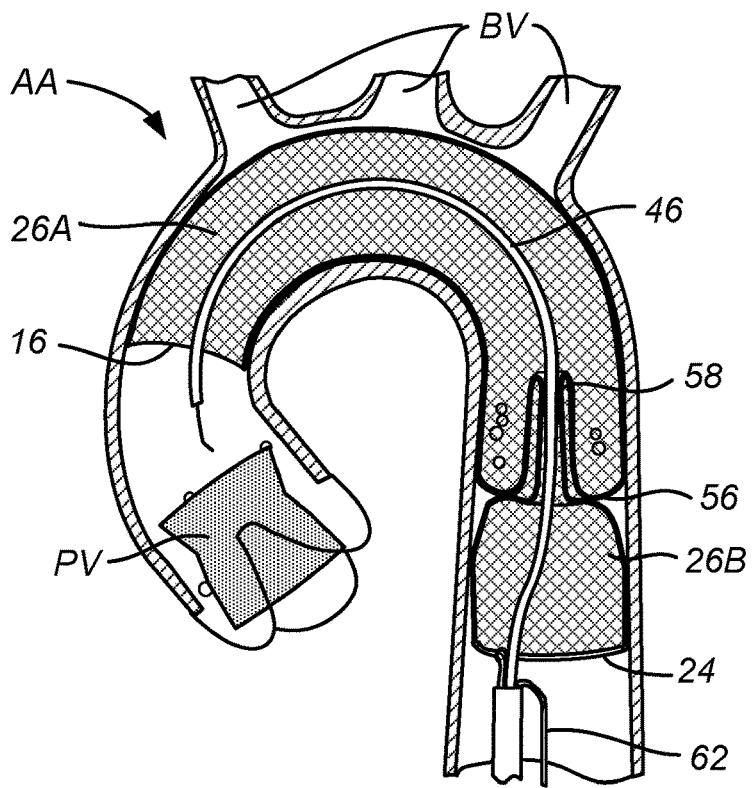
Figure 7U:
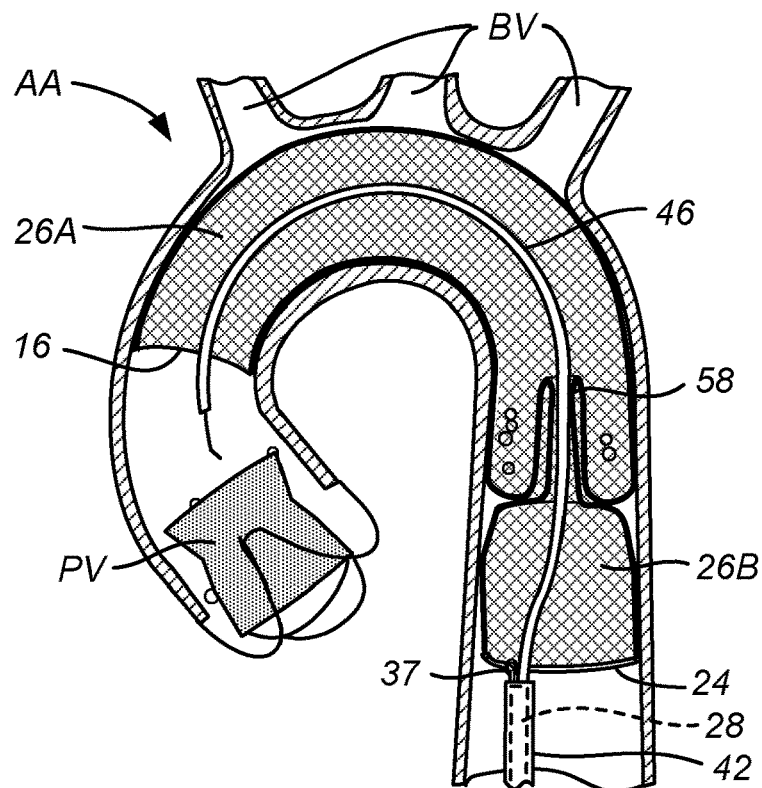
Figure 7V:
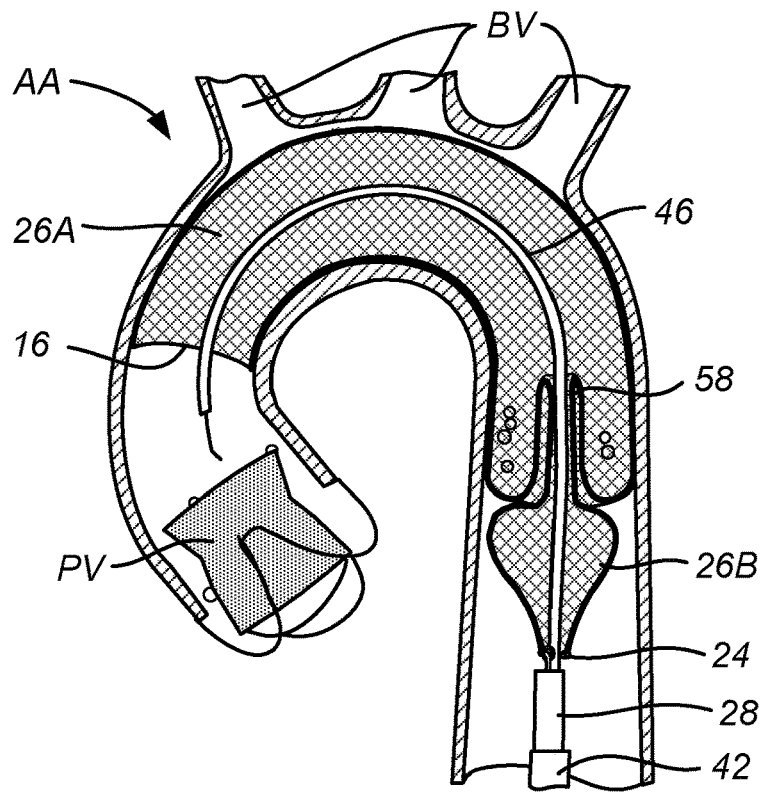
Figure 7W:
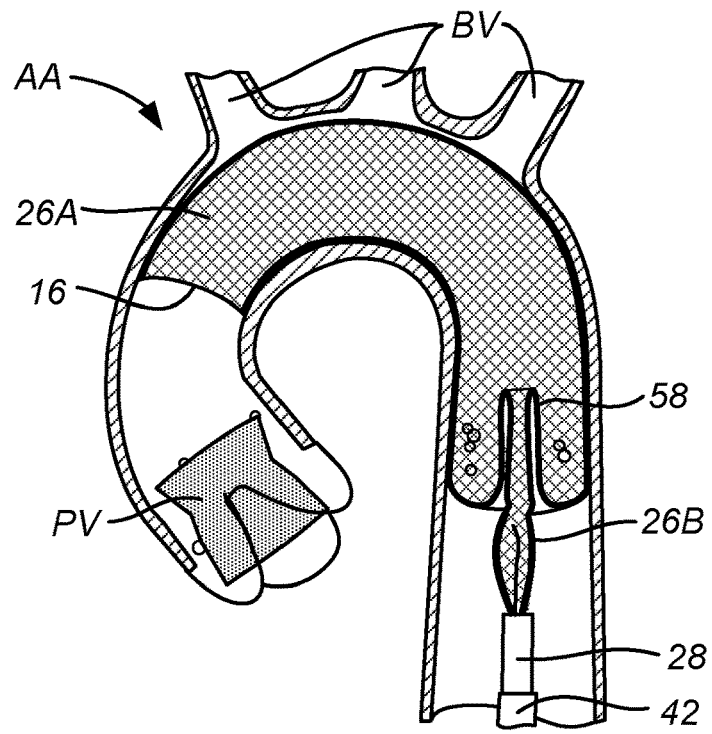
Figure 7X:
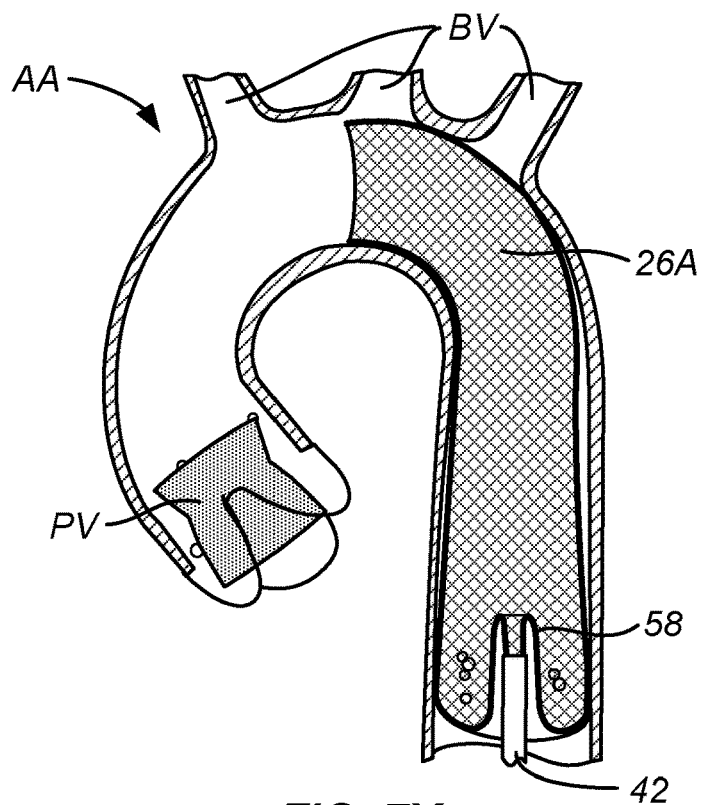
Figure 7Y:
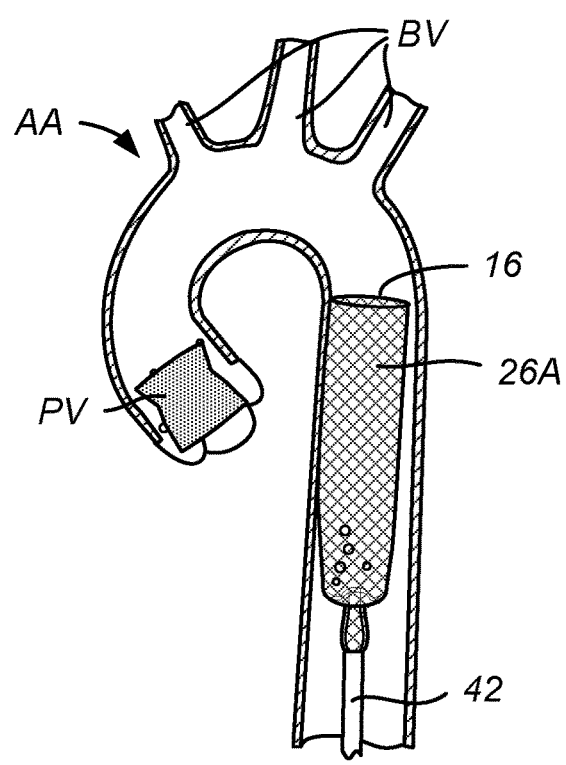
Figure 7Z:
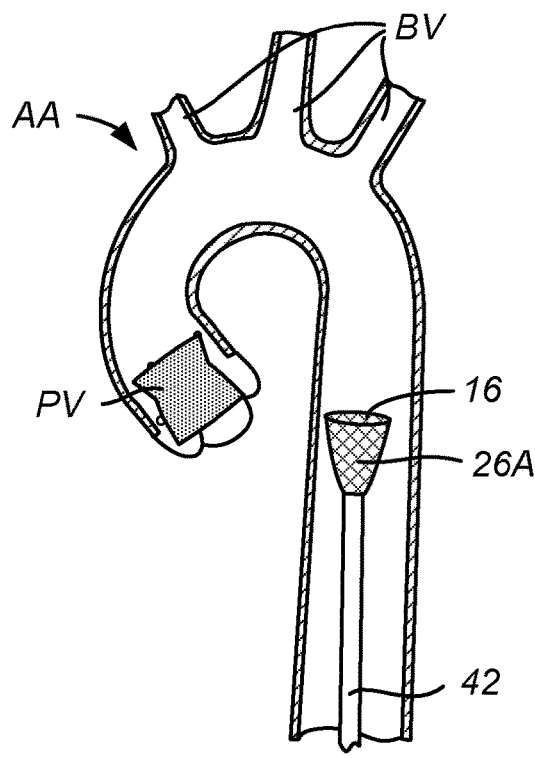
Figure 7Z:
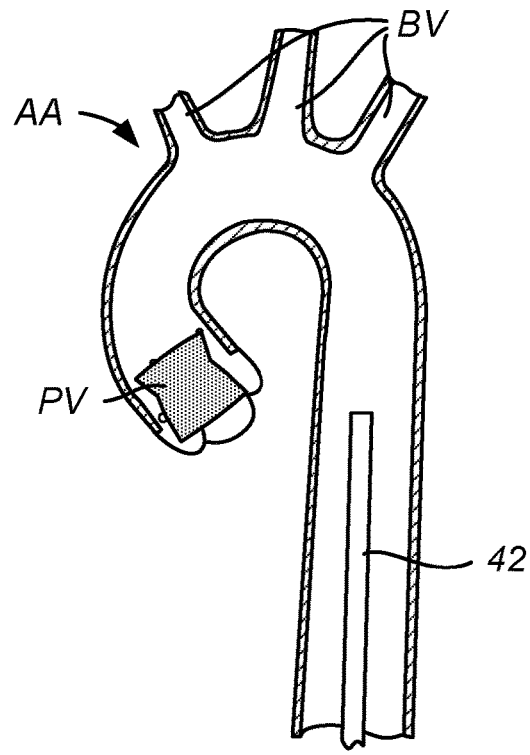

Referring now to FIGS. 7A-7ZZ, a particular protocol for introducing a prosthetic valve PV into the patient's native aortic valve AV will be described. As shown in FIG. 7A, the delivery sheath 42 is initially placed over the guidewire structure 46 as just described with reference to FIG. 6. The catheter body 28 is then advanced through the inner lumen of the delivery sheath 42 such that the radially constrained filter body 12 approaches the open distal end 52 of the delivery sheath.

By then holding the catheter body 28 relatively still or stationary and retracting the delivery sheath 42 in a proximal direction, i.e., away from the patient's aortic valve AV, the distal end of the filter body 12 will be released from constraint so that the tubular porous mesh 14 will begin to radially expand, as shown in FIG. 7B. The delivery sheath 42 continues to be proximally retracted, as shown FIG. 7C, so that the tubular porous mesh 14 expands and engages the inner wall of the ascending aorta immediately above the aortic valve AV. As shown in FIG. 7D, the delivery sheath 42 continues to be proximally withdrawn, allowing the tubular porous mesh 14 to continue to expand and to begin covering the branch vessels BV, with relative full deployment of the upstream cylindrical chamber 26A of the filter body 12 shown in FIG. 7E. As also shown in FIG. 7E, the self-sealing port structure 20 is at its very initial stages of being formed, with further formation being shown in FIG. 7F.

As shown in FIG. 7G, the conical base 56 of what will become the self-sealing port 20 is largely formed, and the downstream cylindrical chamber 26B begins to form as shown in FIG. 7H. The downstream cylindrical chamber 26B is largely formed as shown in FIG. 7I while the self-sealing port 20 is just beginning to form. By then advancing the catheter body 28 in the direction toward the aortic valve AV, as shown in FIG. 7J, a narrowed segment of the tubular porous mesh 14 will begin to invert to form the sleeve structure 58 of the port 20. As also apparent in FIGS. 7I and 7J, the radially collapsible support 24, in the form of the loop 37, opens to open and support the open distal end of the downstream cylindrical chamber 26. It is this support structure 24 which allows the catheter body 28 to manipulate the downstream portion of the filter body 12 so that the downstream cylindrical chamber 26B can be advanced distally or toward the aortic valve AV relative to the upstream cylindrical chamber 26A. The radially expandable/collapsible support 24A will also be useful when retracting the filter body 12 at the end of the procedure, as will be described in more detail below.

The fully deployed self-sealing port 20 is shown in FIG. 7K with the sleeve 58 defining the expandable opening 22 and the conical base 58 facilitating introduction of catheters from the downstream end, as shown in more detail below.

In specific examples, the guidewire structure 46 may include an external support tube which may be retracted and withdrawn to leave the guidewire in place, as shown in FIG. 7L. A diagnostic catheter 60 may then be advanced over the guidewire 46, as shown in FIG. 7M typically being used for angiography. This port 20 will expand to accommodate the diameter of the diagnostic catheter 60 while sealing around the catheter to prevent any emboli from passing through the port.

After withdrawing the diagnostic catheter 60, another guidewire 62 may be introduced for advancing a TAVR delivery catheter 64, as shown in FIG. 7N. The first catheter structure 46 will typically be left in place although it is not visible in FIG. 7N. The TAVR delivery catheter 64 is then advanced over the patient's aortic arch AA, as shown in FIG. 7O, until it passes through the native aortic valve AV, as shown in FIG. 7P. A prosthetic valve PV will then be released from the TAVR catheter 64, as shown in FIG. 7Q. It should be appreciated that during the advancement of the TAVR catheter 64 over the aortic arch AA, and in particular during release of the prosthetic valve PV, there is a substantial risk of emboli being released as the aortic arch and the aortic valve AV may be heavily calcified. If such emboli are present, they will be carried over the aortic arch and through open upstream end 16 of the filter body 12 so that they enter and are contained within the upper cylindrical chamber 26A. In particular, the tubular porous mesh 14 will prevent emboli of any significant size from entering any of the branch vessels BV while allowing blood flow into these vessels. The sleeve 58 of the self-sealing port 20 will conform to and seal around the exterior of the TAVR delivery catheter 64, thus inhibiting or preventing accidental passage of emboli through the port while it is expanded to permit catheter passage.

After the prosthetic valve PV has been released, as shown in FIG. 7Q, the TAVR delivery catheter 64 will be proximally retracted over the guidewire 62, as shown in FIG. 7R. The first guidewire 46 is also shown in FIG. 7R. The TAVR delivery catheter 64 continues to be withdrawn and exits through the self-sealing port 20 which then closes over the guidewire 46, as shown in FIGS. 7S and 7T. The TAVR guidewire 62 is then pulled back through the aorta, as shown in FIG. 7T.

After the TAVR catheter 64 and guidewire 62 have been withdrawn, the prosthetic valve PV is in place and it is necessary to withdraw the filter body 12 from the aortic arch AA. As shown in FIGS. 7U and 7V, the tether structure 32 is manipulated to close the loop 37 of the radially collapsible support 24. In addition to closing the loop 37, the proximal end of the filter structure 12 is drawn to the distal end of the catheter body 28, and the catheter body 28 retracted to draw the filter body into the delivery sheath 42, as shown in FIG. 7W.

The catheter body 28 continues to be proximally withdrawn so that it pulls the downstream cylindrical chamber 26 into the delivery sheath 42, as shown in FIG. 7X, and continues to be proximally withdrawn until the entire filter body 12 is drawn into the delivery sheath 42, as shown in FIGS. 7Y, 7Z, and 7ZZ. The filter body and all emboli contained therein are then safely captured within the delivery sheath 42, and the delivery sheath 42 may be withdrawn from the patient and the procedure may be completed in a conventional manner.

The porous filter mesh material may comprise a variety of knitted, woven or nonwoven fibers, filaments or wires, and will have a pore size chosen to allow blood to pass through but prevent emboli above a certain size from passing through. Suitable materials include resilient metals, such as shape and heat memory alloys, polymers, and combinations thereof, and the materials may optionally have an antithrombogenic coating (such as heparin) on their surfaces. The filter meshes may further incorporate materials and structures to enhance the radiopacity of the filter body. Exemplary materials include gold, platinum, palladium, or tantalum, and other metals having a greater radiopacity than the resilient metals, as well as radiopaque coatings or fillings. In other cases, the resilient metal filaments or wires may be served with thinner, more radiopaque wires or filaments.

The filter body may be constructed in discrete sections that are attached together, but will more typically be formed from a continuous cylindrical mesh structure that is narrowed or folded in sections to form the specific design features, typically consisting of a single such folded tubular mesh structure. Forming the device from one continuous cylindrical mesh allows the filter body to be axially stretched for deployment and/or retrieval, thereby reducing the profile of the filter. Another advantage of a filter formed from a single, continuous tabulate mesh material is that it will contain only smooth, rounded edges. Such edges minimize friction and snagging with catheters and the procedural tools being introduced through the filters.

The self-sealing port may be configured as a conical structure with the access port at its narrow end, typically formed by a sleeve as described previously. In other embodiments, as illustrated below, the self-sealing port may be a simple narrowing of the cylindrical structure, e.g. a self-closing neck region which seal around catheters and other tools introduced therethrough. Whatever the particular geometry, the self-sealing port can be formed by shape-setting a larger, tubular or cylindrical mesh in a reduced diameter via heat treatment or cold forming. In addition, other embodiments of the self-sealing port can be straight, contain a twist, be corrugated, have a flattened section, or possess other features that assist in its ability to close around procedural devices sufficiently to inhibit or prevent emboli from passing through when a catheter is in place. In still other embodiments, the filter body may contain two or more such self-expanding port structures. The port 20 may accommodate a single device (such as a guidewire, catheter, valve delivery system, pacing lead, etc.), two devices or more than two devices simultaneously and can expand and contract to maintain a sufficient seal around multiple devices as needed. Further, such devices can be introduced through the downstream cylindrical chamber 26B and into the port 20 by way of the working lumen 40 of the catheter body 28 or directly by way of a second sheath 50 in an alternative access site, or in some combination thereof.

Referring now to FIGS. 8A-8E, a number of different patterns for forming the tubular porous mesh material 14 of the present invention into a filter body 12 having the self-sealing port 20 between the upstream cylindrical chamber 26A and the downstream cylindrical chamber 26B are illustrated. It will be appreciated that each of the structures in FIGS. 8A-8B begins with a single layer tube of a mesh material as just described. In the configuration of FIG. 8A, the tubular structure is first folded into a bi-layer structure having a fold 14A in its middle. The bi-layer structure is then folded back upon itself and inverted in order to form the illustrated filter body 12a having a structure which is then heat set in the fully radially expanded configuration.

The filter body 12b of FIG. 8B similarly begins as a bi-layer tubular mesh with a single fold 14B at one end. The bi-layer structure is then folded similarly to the pattern of FIG. 8B, except that the open end of cylindrical chamber 26A is folded in an inwardly inverted pattern rather than in a simple fold-back pattern as shown in FIG. 8A.

The filter body 12c illustrated in FIG. 8C is again similar in most respects to the fold pattern of filter 12a of FIG. 8A, except that the open end of the upstream cylindrical chamber 26A has an inner layer folded over an outer layer to form a distal cuff, where the inner layer terminates within the folded-back outer layer.

The filter body 12d illustrated in FIG. 8D is in many ways the inverse of that filter body 12a of FIG. 8A. A single fold 14D in the original single-layer tubular cylinder is located at the open end of the upstream cylindrical chamber 26A. The open downstream end of downstream chamber 26B is folded back on itself to form a cuff structure.

Filter body 12e as illustrated in FIG. 8E is the simplest structure of all where folding of the downstream cylindrical chamber 26B is similar to that in FIGS. 8A-8C, but the open end of the upstream cylindrical chamber 26A terminates with the inner and outer layers open and not folded back at all.

FIG. 9 illustrates a first alternative embodiment of an embolic protection device 70 constructed in accordance with the principles of the present invention. A filter body 72 has an open upstream end 74 and a closed downstream end 76. A self-sealing port 78 is formed in the closed downstream end 76, and a support structure 82 is attached at a downstream end of the filter body. The support structure 82 comprises a pair of struts and can be made of a material (such as a shape memory alloy) that can be compressed for delivery and expanded in situ by the release of a constraining sheath 86. The support is fixedly or movably attached to a deployment catheter body 80 via a collar 84. A distal or upstream end of the catheter body 80 passes through the closed end 76 of the filter body 72 adjacent to the self-sealing port 78.

FIG. 10 illustrates a second alternative embodiment of an embolic protection device 90 constructed in accordance with the principles of the present invention. A filter body 92 with a closed downstream end 93 is attached to a deployment catheter body by fully circumferential support structure 96. The support structure 96 comprises "stent-like" diamond elements over the region where the support structured overlaps and is attached to the mesh material of the filter 92. The support structure 96 is fixedly or movably attached to a deployment catheter body 94 via a collar 100 and a plurality of struts 98. A distal or upstream end of the catheter body 94 passes through the closed end 93 of the filter body 92 adjacent to a self-sealing port 99.

Figure 11:
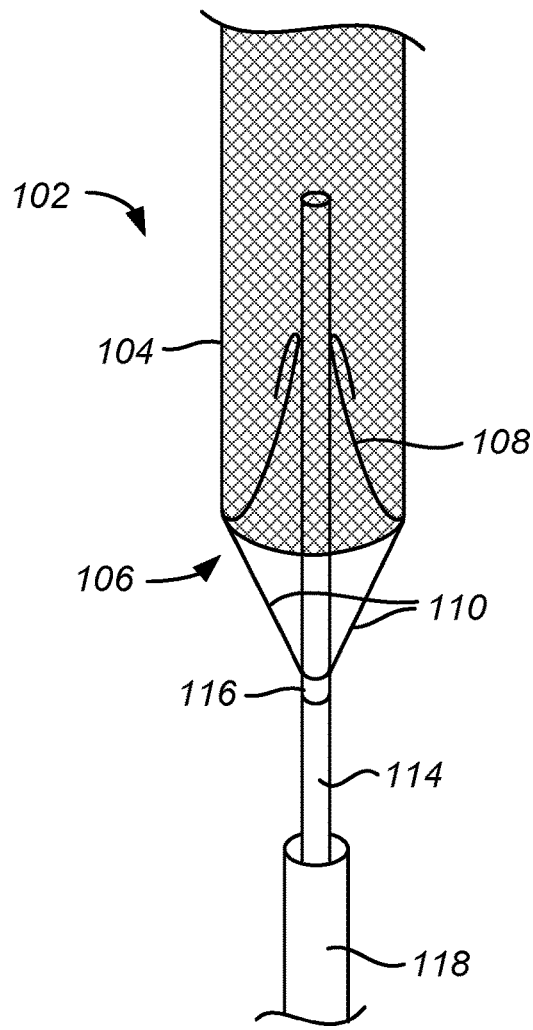
FIG. 11 illustrates a fourth embodiment of an embolic protection device constructed in accordance with the principles of the present invention.
Figure 12:
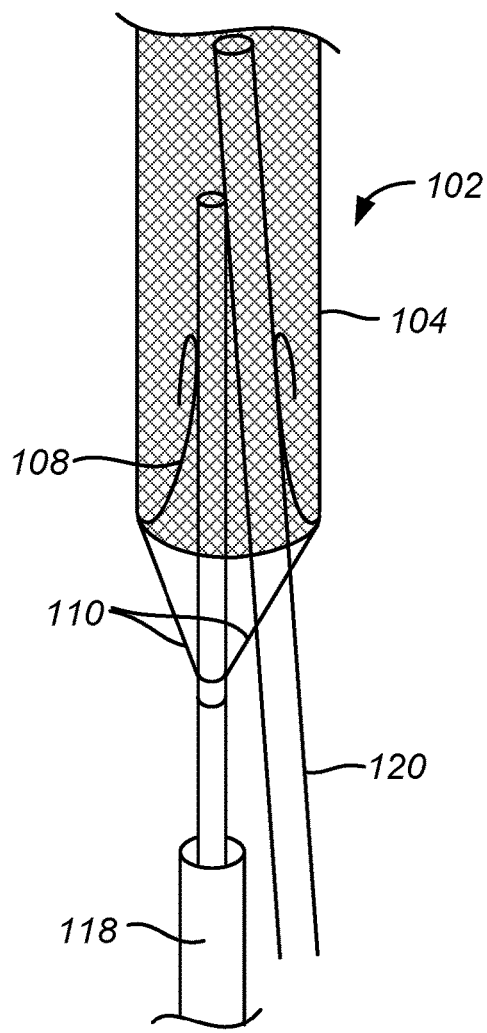
FIG. 12 illustrates use of the device of FIG. 11 for introducing a second working catheter through a self-sealing port of the embolic protection device of FIG. 11.

FIGS. 11 and 12 illustrate a third alternate embodiment of an embolic protection device 102 having a conical mesh self-sealing port 108 in a closed end 106 of a filter body 104. A deployment catheter body 114 is attached by a collar 116. A delivery sheath 118 is provided for delivery and traction of the filter body 104. In FIG. 11, a distal or upstream end of the catheter body 114 is disposed through the self-sealing port 108 and provides an introductory lumen or other path through the port adjacent to the self-sealing port 108. In FIG. 12, a TAVR delivery or other working catheter is introduced through the self-sealing port in parallel to the catheter body 114. The periphery of the self-sealing port 108 will be sufficiently compliant (elastic) to conform to and seal against both catheters simultaneously.

FIGS. 13A-13C illustrate a fourth alternative embodiment of an embolic protection device 130 constructed in accordance with the principles of the present invention. A filter body 132 comprises a double layer of mesh throughout most of the filter, with an additional layer or cuff 150 (for a total of three layers) at a downstream end to increase the anchoring strength of the filter in this portion of the device. FIG. 13A shows the embolic protection device 130 in its relaxed configuration, while FIGS. 13B and 13C show the embolic protection device 130 as it is axially stretched in the direction of arrows 146 into a delivery or retrieval configuration. Since a self-sealing port 134 and other device features are integrally or monolithically formed within a continuous cylindrical mesh structure, these features effectively disappear when the filter body 132 is fully stretched out in the axial direction. This ability to stretch out and eliminate internal structure minimizes the device profile. The construction of the filter from one continuous cylindrical surface also avoids manufacturing complexity and maintains a smooth contact surface throughout the device to reduce the friction of procedural tools passing through the filter. The filter body is attached to a deployment catheter body 144 by a stent-like peripheral support structure 140 which overlaps or overlies a downstream cylindrical chamber 139 of the filter body 132. The self-sealing port 134 may comprise a conical base 136 and a sleeve 138 generally as described previously.

Figure 14:
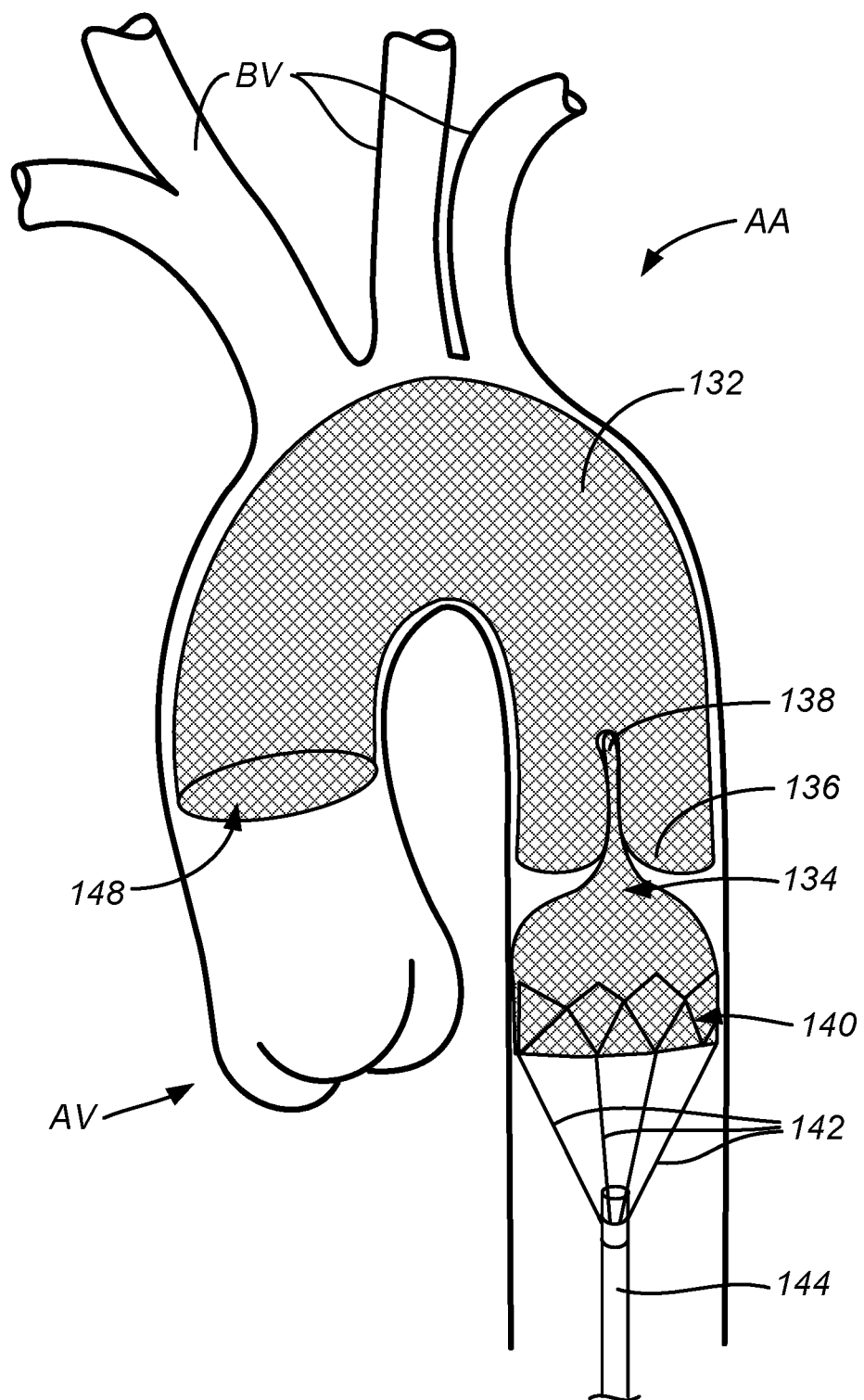
FIG. 14 illustrates placement of a sixth embodiment of an embolic protection device constructed in accordance with the principles of the present invention over a patient's aortic arch.

FIG. 14 illustrates the embolic protection device 130 deployed over a patient's aortic arch to protect the branch vessels as an interventional catheter is delivered in an upstream direction through the self-sealing port 134 to perform a procedure, such as valvuloplasty or TAVR, at the aortic valve AV.

Figure 15A:
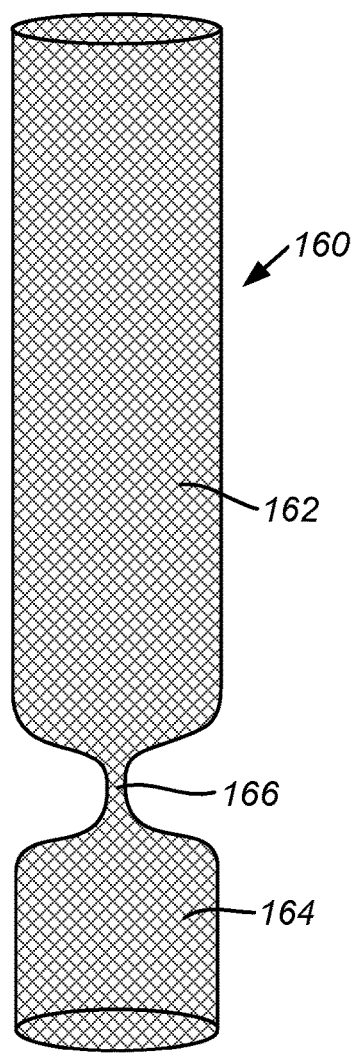
FIGS. 15A-15C illustrate different folding patterns which can be used to provide self-sealing ports in the filter bodies of the present invention.
Figure 15B:
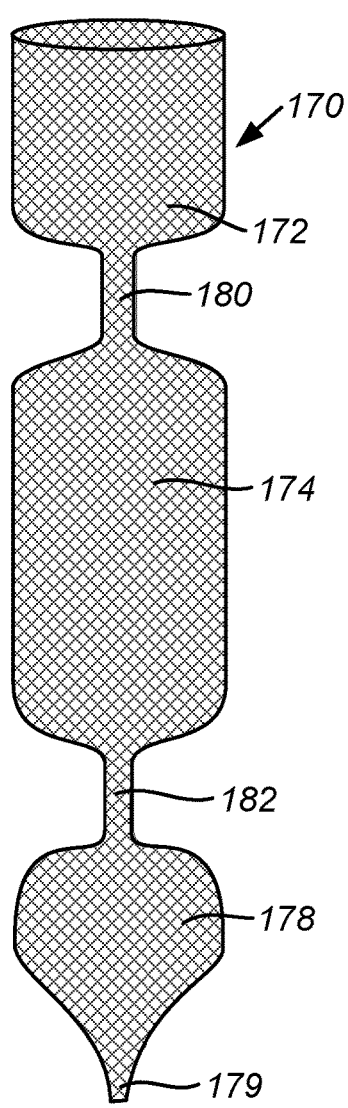
Figure 15C:
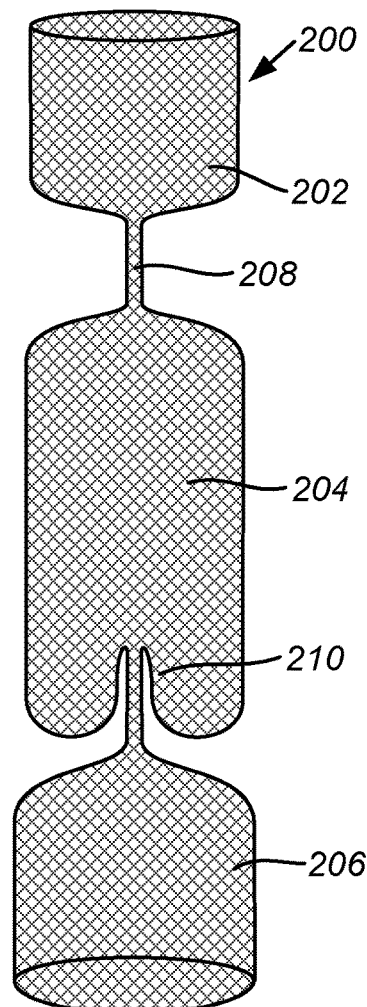

FIGS. 15A-15C shows alternative configurations of the filter body of the present invention. FIG. 15A shows a filter body 160 comprising an upstream cylindrical chamber 162 and a downstream cylindrical chamber 164 separated by a simple narrowing or neck 166 formed in the cylindrical mesh material. The cylindrical mesh material may be single-walled, double-walled, have more than two layers over some or all of the wall area, or combinations thereof, and this filter body configuration can be combined in most or all of the embodiments of the embolic protection devices of the present invention described previously.

FIG. 15B shows a filter body 170 comprising an upstream cylindrical chamber 172, a central cylindrical chamber 174, and a downstream cylindrical chamber 178 separated by a necks 180 and 182, respectively. It will be appreciated that such multiple cylindrical chambers could be separated by any of the self-closing port structures described previously. The downstream end of the downstream cylindrical chamber 178 may be gathered or closed, as illustrated, and the filter body 170 with a closed downstream end may find particular use in the clot capture configurations described in FIGS. 16A-16E below. As with previous embodiments, the cylindrical mesh material of filter body 170 may be single-walled, double-walled, have more than two layers, or be combinations thereof, and multi-chamber filter body configurations can be combined in most or all of the embodiments of the embolic protection devices of the present invention described previously, although the downstream end of the downstream chamber will have to be opened.

FIG. 15C shows a filter body 200 comprising an upstream cylindrical chamber 202, a central cylindrical chamber 204, and a downstream cylindrical chamber 206 separated by a neck 208 and a self-sealing port 210, respectively. The downstream end of the downstream cylindrical chamber 206 is open, and the multi-chamber filter body 200 can be combined in most or all of the embodiments of the embolic protection devices of the present invention described previously. The cylindrical mesh material of filter body 200 may be single-walled, double-walled, have more than two layers, or be combinations thereof.

Figure 16A:
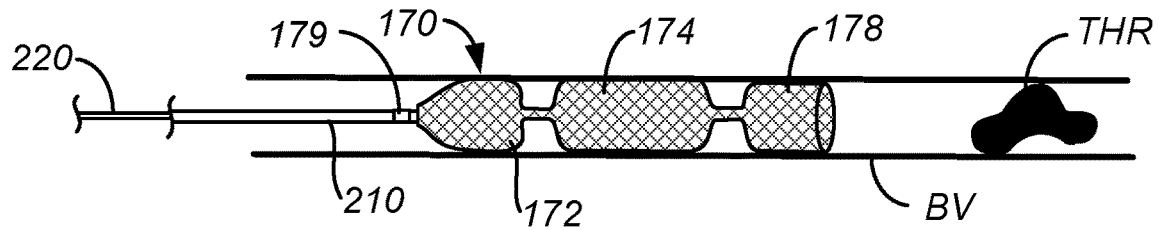
FIGS. 16A-16E illustrate the use of a filter body similar to that shown in FIG. 15B for capturing clot in a second exemplary method of the present invention.
Figure 16B:
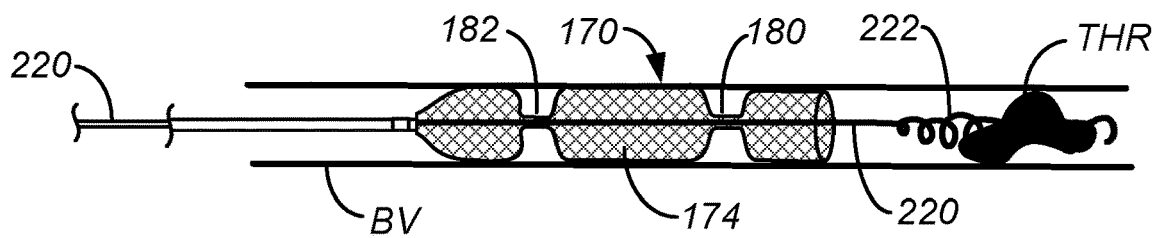
Figure 16C:
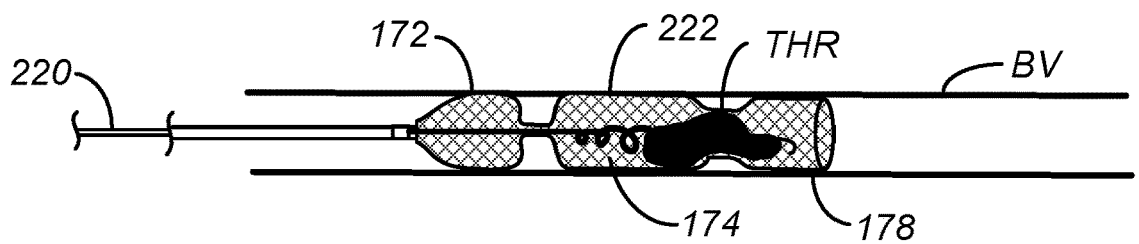
Figure 16D:
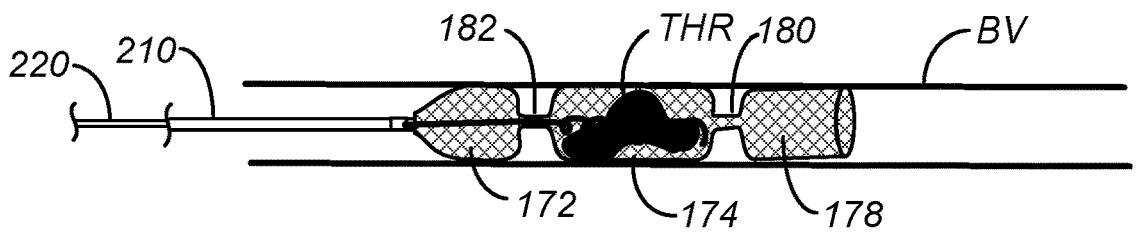
Figure 16E:
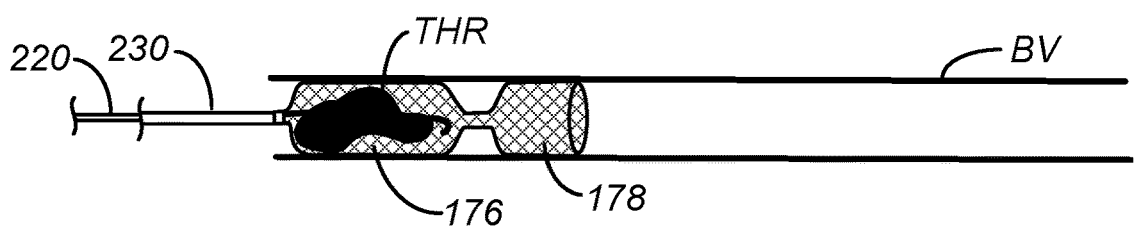

FIGS. 16A-16E show a specific procedural using the filter body 170 of FIG. 15B for capturing clot and/or thrombus in a cardiac, peripheral, or cerebral blood vessel BV. Such devices and protocols will be particularly useful for clot/thrombus retrieval in a cranial vessel to treat acute ischemic stroke. As shown in FIG. 16A, the gathered end 179 of the filter body 170 is attached to a distal end of a deployment catheter 210, and the catheter 210 is advanced through a microcatheter 230 (FIG. 16E). A clot capture catheter 220, such as a Merci® retriever catheter, having a clot capture element 222, such as a helical tip at its distal end is advanced through the catheter 220, the filter body 170, and into the clot/thrombus THR, as shown in FIG. 16B. The clot capture catheter 220 is then pulled proximally to draw the clot/thrombus THR through neck 180 into the central chamber 174, as shown in FIGS. 16B-16D. After the clot/thrombus THR is in the central chamber 174, the chance that it will be lost from the filter is greatly reduced, and any emboli which might escape through the necks 180 and 182 will likely be captured in the upstream and downstream cylindrical chambers 178 and 172, respectively. The upstream neck 180 will be configured to stretch open to allow the clot retrieval device and the ensnared thrombus and clot to pass through, and to close after the clot and/or thrombus are fully enclosed within the central cylindrical chamber 174. Any debris that may come loose from the clot and thrombus is contained by the fully-closed necks 180 and 182 (FIG. 16D), the assembly of the clot retriever 220, the filter body 170, and catheter body 220 may be safely withdrawn through the microcatheter 230.

Modification of the above-described assemblies and methods for carrying out the invention, combinations between different variations as practicable, and variations of aspects of the invention that are obvious to those of skill in the art are intended to be within the scope of the invention disclosure.

What is claimed is:

1. An embolic protection device, said device comprising:
    a filter body comprising a single wall tubular porous mesh having an open upstream end, an open downstream end, and a port disposed on an upstream side of the open downstream end, wherein a portion of said single-wall tubular porous mesh is folded to form said port comprising an expandable opening configured to conform to at least one working catheter passing therethrough;
    a radially collapsible and expandable support comprising a wire loop attached about a periphery of the downstream end of the filter body;
    a catheter body having a distal end coupled to the radially collapsible and expandable support; and
    a delivery sheath having a lumen configured to receive and radially constrain the filter body;
    wherein the catheter body may be distally advanced relative to the delivery sheath to release the filter body from constraint and to allow the filter body to radially expand and wherein the catheter body may be proximally retracted relative to the delivery sheath to reposition the support and filter body back into the lumen of the delivery sheath such that the support radially collapses the downstream end of the filter body prior to the filter body being repositioned within the lumen.

2. An embolic protection device as in claim 1, wherein the wire loop is secured around the entire periphery of the downstream end of the filter body.

3. An embolic protection device as in claim 2, wherein the catheter body has at least one deployment lumen which receives a tether attached to the loop.

4. An embolic protection device as in claim 3, wherein the loop is configured as a lasso to allow the tether to draw the open downstream end of the filter body closed prior to drawing the filter body into the lumen of the delivery sheath.

5. An embolic protection device as in claim 1, wherein the open upstream end of the filter body is defined by the periphery of the open upstream chamber.

6. An embolic protection device as in claim 1, wherein the folded wall portion of the tubular porous mesh comprises a resiliently closed sleeve portion extending in an upstream direction from an apex of a conical opening which defines the expandable opening of the port.

7. An embolic protection device as in claim 1, wherein the folded wall portion of the tubular porous mesh material which is configured to radially collapse to define an expandable opening of the port.

8. An embolic protection device as in claim 1, wherein the catheter body includes at least a working catheter lumen for advancing a working catheter therethrough, into the open downstream end of the filter body, and through the port.

9. An embolic protection device as in claim 8, wherein the catheter body further includes at least a deployment lumen which receives a tether attached to the radially collapsible support.

10. An embolic protection device as in claim 1, wherein the port comprises a self-sealing port.

11. An embolic protection device as in claim 1, wherein the port is spaced inwardly from each of said ends of the filter body.

12. An embolic protection device as in claim 1, wherein the port inverts radially inwardly as other wall portions expand when released from radial constraint from the delivery sheath.

13. An embolic protection device as in claim 1, wherein the folded wall portion forms the port with a conical opening on the downstream side.

14. An embolic protection device as in claim 1, wherein the catheter body is configured to be pushed distally to release the filter body from constraint within the delivery sheath and to allow the filter body to radially expand and wherein the catheter body is configured to be pulled to proximally to reposition the support and filter body within the lumen of the delivery sheath.

15. An embolic protection device as in claim 1, wherein the single-wall tubular porous mesh comprises a single layer.

16. An embolic protection device as in claim 1, wherein the single-wall tubular porous mesh comprises two or more layers.

17. An embolic protection device, said device comprising:
a filter body comprising a tubular porous mesh having an open upstream end, an open downstream end, and a port disposed inside of the tubular porous mesh on an upstream side of the open downstream end, said port comprising an expandable opening configured to conform to at least one working catheter passing therethrough;
a radially collapsible and expandable support coupled to a periphery of the downstream end of the filter body;
a catheter body having a distal end coupled to the radially collapsible and expandable support; and
a delivery sheath having a lumen configured to receive and radially constrain the filter body;
wherein the catheter body may be distally advanced relative to the delivery sheath to release the filter body from constraint and to allow the filter body to radially expand with the support circumscribing the downstream end of the filter body and wherein the catheter body may be proximally retracted relative to the delivery sheath to pull the support and filter body back into the lumen of the delivery sheath such that the support body being drawn into the lumen; and
wherein the port comprises an inverted portion of the tubular porous mesh which is inverted radially inwardly to the inside of the filter body; and
wherein an inverted wall portion of the tubular porous mesh has a resiliently closed sleeve portion extending in an upstream direction from an apex of a conical opening which defines the expandable opening of the port.

18. An embolic protection device, said device comprising:
a filter body comprising a tubular porous mesh having an open upstream end, an open downstream end, and a port disposed inside of the tubular porous mesh on an upstream side of the open downstream end, said port comprising an expandable opening configured to conform to at least one working catheter passing therethrough;
a radially collapsible and expandable support coupled to a periphery of the downstream end of the filter body;
a catheter body having a distal end coupled to the radially collapsible and expandable support; and
a delivery sheath having a lumen configured to receive and radially constrain the filter body;
wherein the catheter body may be distally advanced relative to the delivery sheath to release the filter body from constraint and to allow the filter body to radially expand with the support circumscribing the downstream end of the filter body and wherein the catheter body may be proximally retracted relative to the delivery sheath to pull the support and filter body back into the lumen of the delivery sheath such that the support body being drawn into the lumen; and
wherein the port comprises an inverted portion of the tubular porous mesh which is inverted radially inwardly to the inside of the filter body; and
wherein the inverted wall portion forms the port with a conical opening on the downstream side.

* * * * *